US010261151B2

(12) United States Patent
Driehuys et al.

(10) Patent No.: US 10,261,151 B2
(45) Date of Patent: *Apr. 16, 2019

(54) SYSTEMS AND METHODS FOR ASSESSING PULMONARY GAS TRANSFER USING HYPERPOLARIZED $^{129}$XE MRI

(71) Applicant: Duke University, Durham, NC (US)

(72) Inventors: Bastiaan Driehuys, Chapel Hill, NC (US); Gary Price Cofer, Hillsborough, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/447,321

(22) Filed: Mar. 2, 2017

(65) Prior Publication Data

US 2017/0176559 A1 Jun. 22, 2017

Related U.S. Application Data

(62) Division of application No. 14/535,990, filed on Nov. 7, 2014, now Pat. No. 9,625,550, which is a division of application No. 11/866,552, filed on Oct. 3, 2007, now Pat. No. 8,911,709.

(60) Provisional application No. 60/827,983, filed on Oct. 3, 2006.

(51) Int. Cl.
| *A61B 5/00* | (2006.01) |
| *A61B 5/08* | (2006.01) |
| *A61B 5/055* | (2006.01) |
| *A61B 5/107* | (2006.01) |
| *G01R 33/34* | (2006.01) |
| *G01R 33/48* | (2006.01) |
| *G01R 33/56* | (2006.01) |
| *G01R 33/483* | (2006.01) |
| *G01R 33/563* | (2006.01) |
| *G01R 33/465* | (2006.01) |
| *G01N 24/08* | (2006.01) |

(52) U.S. Cl.
CPC ............ *G01R 33/483* (2013.01); *A61B 5/055* (2013.01); *A61B 5/08* (2013.01); *A61B 5/1075* (2013.01); *G01R 33/34076* (2013.01); *G01R 33/465* (2013.01); *G01R 33/4816* (2013.01); *G01R 33/5601* (2013.01); *G01R 33/56341* (2013.01); *A61B 5/416* (2013.01); *A61B 5/4887* (2013.01); *A61B 5/7239* (2013.01); *G01N 24/08* (2013.01)

(58) Field of Classification Search
None
See application file for complete search history.

(56) References Cited

U.S. PATENT DOCUMENTS

| 4,901,019 | A | 2/1990 | Wedeen |
| 4,949,042 | A | 8/1990 | Kuhara et al. |
| 5,271,401 | A | 12/1993 | Fishman |
| 5,374,890 | A | 12/1994 | Zou et al. |
| 6,211,677 | B1 | 4/2001 | Burl et al. |
| 6,263,228 | B1 | 7/2001 | Zhang et al. |
| 6,426,058 | B1 | 7/2002 | Pines et al. |
| 7,550,970 | B2 | 6/2009 | Servin et al. |
| 7,805,176 | B2 | 9/2010 | Ruppert et al. |
| 8,911,709 | B2* | 12/2014 | Driehuys ............... A61B 5/055 424/9.3 |
| 2001/0000727 | A1 | 5/2001 | Driehuys et al. |
| 2001/0037063 | A1 | 11/2001 | Albert et al. |
| 2001/0041834 | A1 | 11/2001 | Mugler, III et al. |
| 2002/0006382 | A1 | 1/2002 | Driehuys et al. |
| 2003/0064023 | A1 | 4/2003 | Driehuys et al. |
| 2003/0064024 | A1* | 4/2003 | Driehuys ............... A61B 5/055 424/9.3 |
| 2004/0005273 | A1* | 1/2004 | Driehuys ............... A61B 5/055 424/9.3 |
| 2004/0032977 | A1 | 2/2004 | Blezek et al. |
| 2004/0230113 | A1 | 11/2004 | Bolam et al. |
| 2004/0260173 | A1 | 12/2004 | Salerno et al. |
| 2005/0054914 | A1 | 3/2005 | Duerk et al. |
| 2005/0165296 | A1 | 7/2005 | Ma |

FOREIGN PATENT DOCUMENTS

| EP | 1 286 171 A2 | 2/2003 |
| JP | 2006-087763 | 4/2006 |
| RU | 2248011 | 1/2005 |

(Continued)

OTHER PUBLICATIONS

B Driehuys, GP Cofer, J Pollaro, JB Mackel, LW Hedlund, GA Johnson. "Imaging alveolar—capillary gas transfer using hyperpolarized 129Xe MRI." Proceedings of the National Academy of Sciences, vol. 103 No. 48, Nov. 28, 2006, pp. 18278-18283. (Year: 2006).*

J Wang, AJ Wright, D-e Hu, R Hesketh, KM Brindle. "Single Shot Three-Dimensional Pulse Sequence for Hyperpolarized 13C MRI." Magnetic Resonance in Medicine, vol. 77, 2017, pp. 740-752. (Year: 2017).*

Abdeen et al., "Measurement of Xenon Diffusing Capacity in the Rat Lung by Hyperpolarized $^{129}$Xe MRI and Dynamic Spectroscopy in a Single Breath-Hold", *Magnetic Resonance in Medicine*, 2006, 56: 255-264.

Brady, Michael "Basics of MRI" www.robots.ox.ac.uk/~jmb/lectures/medimanalecture1.pdf Accessed online Nov. 29, 2016 (44 pages) (written in 2004).

(Continued)

*Primary Examiner* — Isaac Shomer
(74) *Attorney, Agent, or Firm* — Myers Bigel, P.A.

(57) ABSTRACT

Methods and systems for assessing pulmonary gas exchange and/or alveolar-capillary barrier status include obtaining at least one MRI image and/or image data of $^{129}$Xe dissolved in the red blood cells (RBC) in the gas exchange regions of the lungs of a patient. The image is sufficiently sensitive to allow a clinician or image recognition program to assess at least one of pulmonary gas exchange, barrier thickness or barrier function based on the $^{129}$Xe MRI RBC image.

17 Claims, 12 Drawing Sheets

(56) References Cited

FOREIGN PATENT DOCUMENTS

WO    WO 99/35508    7/1999

OTHER PUBLICATIONS

Butler et al., "Measuring surface-area-to-volume ratios in soft porous materials using laser-polarized xenon interphase exchange nuclear magnetic resonance", *Journal of Physics: Condensed Matter*, 2002, 14: L297-L304.
Cleveland et al., "Hyperpolarized $^{129}$Xe MR Imaging of Alveolar Gas Uptake in Humans", *PLoS One*, 2010, 5(8): pp. 1-8, e12192.
Driehuys et al., "Imaging alveolar—capillary gas transfer using hyperpolarized $^{129}$Xe MRI", *PNAS*, 2006, 103(48): 18278-18283.
Driehuys et al., "Imaging Pulmonary Gas Exchange Using Hyperpolarized $^{129}$Xe", *Proceedings of the International Society for Magnetic Resonance in Medicine*, 2006, 14: p. 862.
Flask, Christopher Alan, "Rapid Dixon Acquisitions for Water/Lipid Separation in MRI", *Case Western Reserve University PhD Thesis*, Jan. 2005, pp. 1-136 and four cover pages.
Glover et al., "Three-Point Dixon Technique for True Water/Fat Decomposition with $B_0$ Inhomogeneity Correction", *Magnetic Resonance in Medicine*,1991, 18: 371-383.
Golman et al., "Molecular imaging using hyperpolarized $^{13}$C", *The British Journal of Radiology*, 2003, 76: S118-S127.
Hatabu et al., "T2* and proton density measurement of normal human lung parenchyma using submillisecond echo time gradient echo magnetic resonance imaging"*European Journal of Radiology*, 1999, 29: 245-252.
Hornak, J.P., "The Basics of MRI", *Fast Imaging Techniques*, 1996-2010, Chapter 12, pp. 1-5.
International Search Report and the Written Opinion of the International Searching Authority Corresponding to International Application No. PCT/US2007/21155; filed Oct. 2, 2007.
Mansson et al., "Characterization of Diffusing Capacity and Perfusion of the Rat Lung in a Lipopolysaccaride Disease Model Using Hyperpolarized $^{129}$Xe", *Magnetic Resonance in Medicine*, 2003, 50: 1170-1179.
Pavlin, Tina, "Hyperpolarized Gas Polarimetry and Imaging at Low Magnetic Field", *California Institute of Technology PhD Thesis*, 2003, pp. i-xix and 1-165.
Ruppert et al., "NMR of hyperpolarized $^{129}$Xe in the canine chest: spectral dynamics during a breath-hold", *NMR in Biomedicine*, 2000, 13: 220-228.
Ruppert et al., "Probing Lung Physiology With Xenon Polarization Transfer Contrast (XTC)", *Magnetic Resonance in Medicine*, 2000, 44: 349-357.
Ruppert et al., "Exploring Lung Function With Hyperpolarized $^{129}$Xe Nuclear Magnetic Resonance", *Magnetic Resonance in Medicine*, 2004, 51: 676-687.
Ruset, Iulian C., "Hyperpolarized $^{129}$Xe Production and Applications", *University of New Hampshire PhD Dissertation*, May 2005, pp. i-xxii and 1-152.
Skinner et al., "An Extended Two-Point Dixon Algorithm for Calculating Separate Water, Fat, and *B0* Images", *MRM*, 1997, 37: 628-630.
Song et al., "Improving Non-Cartesian MRI Reconstruction through Discontinuity Subtraction", *International Journal of Biomedical Imaging*, 2006, pp. 1-9.
Spuentrup et al., "Free-breathing 3D Steady-State Free Precession Coronary MR Angiography with Radial k-Space Sampling: Comparison with Cartesian k-Space Sampling and Cartesian Gradient-Echo Coronary MR Angiography—Pilot Study", *Radiology*, 2004, 231(2): 581-586.
Supplementary European Search Report and European Search Opinion Corresponding to European Application No. EP 07 83 9139, dated Jan. 3, 2010.
Swanson et al., "Brain MRI with Laser-Polarized $^{129}$Xe", *MRM*, 1997, 38: 695-698.
Swanson et al., "Distribution and Dynamics of Laser-Polarized $^{129}$Xe Magnetization in Vivo", *Magnetic Resonance in Medicine*, 1999, 42: 1137-1145.
Wild et al., "Comparison Between 2D and 3D Gradient-Echo Sequences for MRI of Human Lung Ventilation With Hyperpolarized $^3$He", *Magnetic Resonance in Medicine*, 2004, 52: 673-678.
Albert et al. "Biological magnetic resonance Imaging using laser-polarized $^{129}$Xe" *Nature* 370:199-201 (1994).
European Examination Report corresponding to related European Patent Application No. 07 839 139.8 (8 pages) (dated May 14, 2018).
Mugler III et al. "MR Imaging and Spectroscopy Using Hyperpolarized $^{129}$Xe Gas: Preliminary Human Results" *Magnetic Resonance in Medicine* 37(6):809-815 (1997).
European Examination Report Corresponding to European Patent Application No. 07 839 139.8; dated Jan. 12, 2017; 8 Pages.
Driehuys et al. "Real-time Production and in vivo Imaging of Hyperpolarized $^{129}$Xe", *Proc. Intl. Soc. Mag. Reson. Med.*, 14 (2006), p. 861.

\* cited by examiner

© 2006 DUKE UNIVERSITY

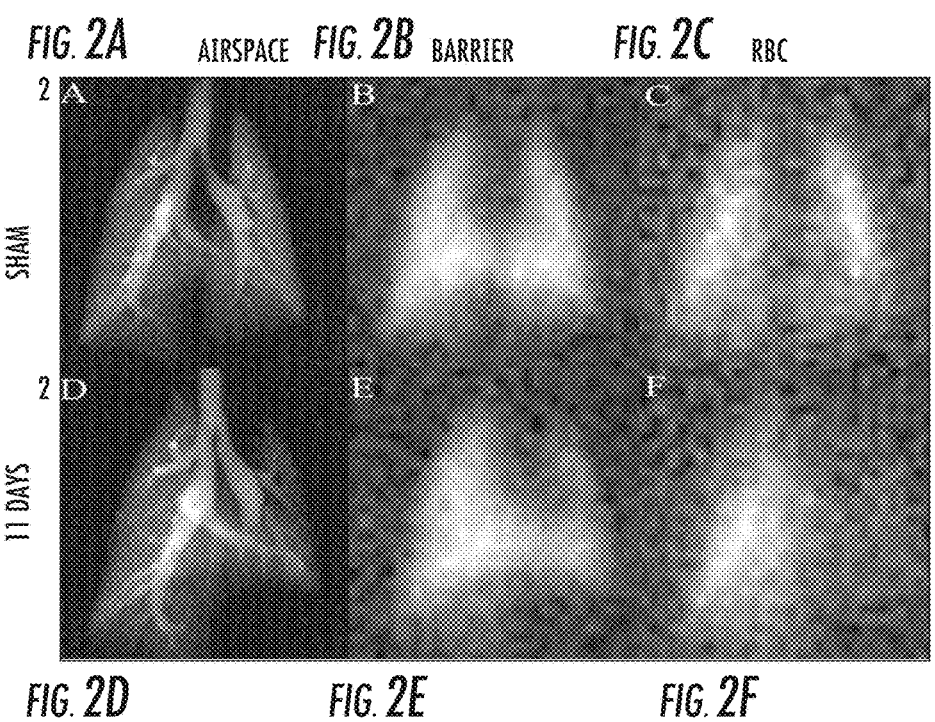

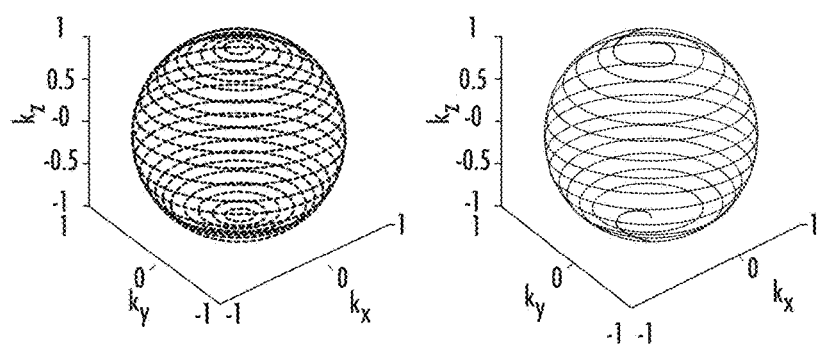
FIG. 10A
FIG. 10B
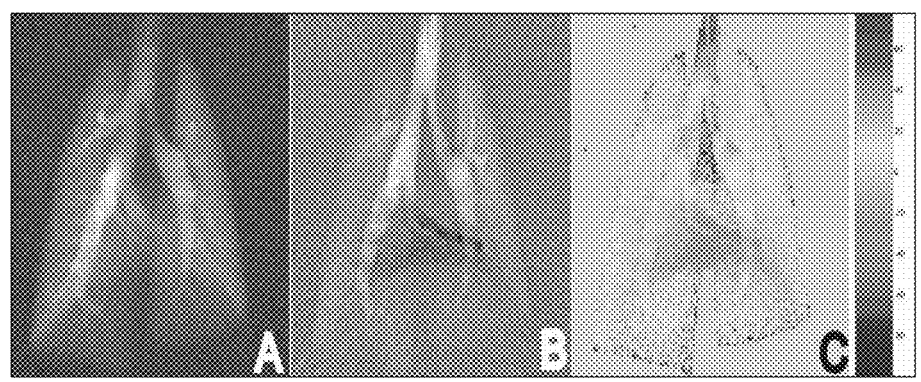
FIG. 11A   FIG. 11B   FIG. 11C

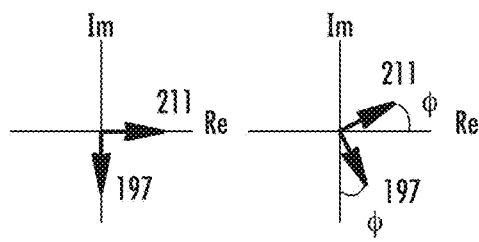
FIG. 12A     FIG. 12B
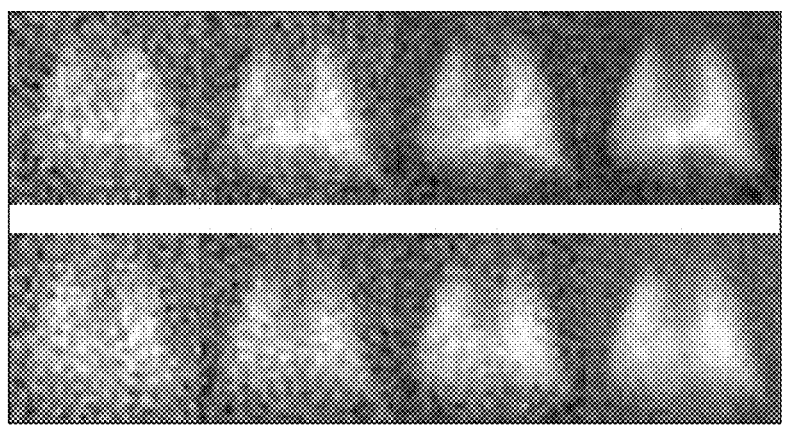
FIG. 13A
BARRIER
FIG. 13B
RBC

SYSTEMS AND METHODS FOR ASSESSING PULMONARY GAS TRANSFER USING HYPERPOLARIZED $^{129}$XE MRI

RELATED APPLICATIONS

This application is a divisional application of U.S. patent application Ser. No. 14/535,990, filed Nov. 7, 2014, which is a divisional application of U.S. patent application Ser. No. 11/866,552, filed Oct. 3, 2007, now U.S. Pat. No. 8,911,709, issued Dec. 16, 2014, which claims the benefit of and priority to U.S. Provisional Application Ser. No. 60/827,983, filed Oct. 3, 2006, the contents of which are hereby incorporated by reference as if recited in full herein.

GOVERNMENT GRANTS

The invention was carried out using government grants including a grant from the NCRR/NCI National Biomedical Technology Resource Center (P41 RR005959/R24 CA 092656) and a grant from the National Institutes of Health, NIH/NHLBI (R01 HL055348). The United States government has certain rights to this invention.

RESERVATION OF COPYRIGHT

A portion of the disclosure of this patent document contains material to which a claim of copyright protection is made. The copyright owner has no objection to the facsimile or reproduction by anyone of the patent document or the patent disclosure, as it appears in the Patent and Trademark Office patent file or records, but reserves all other rights whatsoever.

FIELD OF THE INVENTION

The invention relates to NMR spectroscopy and MRI (Magnetic Resonance Imaging).

BACKGROUND OF THE INVENTION

The exchange of gases in the lung requires ventilation, perfusion and the diffusion of gases across the blood-gas barrier of the alveoli. While pulmonary ventilation (1, 2) and perfusion (3, 4) can be examined by a variety of imaging techniques, currently no methods exist to image alveolar-capillary gas transfer. Unfortunately, certain pulmonary pathologies such as, for example, inflammation, fibrosis, and edema may initially have a predominant effect on the gas exchange process, but not ventilation or perfusion. The degree to which a "diffusion block" (5) is present or absent in the blood-gas barrier has been difficult to determine in studies to date (6). In healthy alveoli, the harmonic mean thickness [as defined by Weibel (7) of the blood-gas barrier is about 0.77 μm and oxygen traverses this space in less than a millisecond, saturating the red blood cells (RBCs) in tens of milliseconds. However, in regions where the barrier is thickened, oxygen may be undesirably prevented from diffusing across the barrier fast enough to saturate the RBCs before they exit the gas exchange region [estimated at about 750 ms in humans (5), 300 ms in rats (8).

SUMMARY OF EMBODIMENTS OF THE INVENTION

Embodiments of the present invention provide systems and methods to non-invasively obtain spectra or image data associated with alveolar-capillary gas transfer using hyperpolarized $^{129}$Xe. The images can be direct images that visually reflect the barrier's ability (or inability) to transfer gas to red blood cells.

Embodiments of the invention provide images that can be useful to diagnose lung diseases or injury, study or evaluate interstitial lung diseases or injury and/or the progression or abatement thereof, and/or evaluate the efficacy of directed therapies the side effects or the inadvertent negative effects of therapies or drug treatments on alveolar-capillary gas transfer.

Some embodiments are directed to methods for assessing pulmonary gas exchange and/or alveolar-capillary barrier status. The methods include: (a) transmitting an RF MRI excitation pulse sequence configured to excite dissolved phase hyperpolarized $^{129}$Xe in a gas exchange region of a lung of a subject; and (b) obtaining image data of a dissolved phase $^{129}$Xe MRI red blood cell (RBC) compartment in the gas exchange region of the lung of the subject based on the transmission.

The obtained at least one $^{129}$Xe MRI RBC image may be obtained using a RF pulse repetition time of between about 10-200 ms, typically between about 10-60 ms, and more typically between about 10-50 ms and optionally a large angle excitation pulse (such as about 90 degrees).

The obtained image may be used to assess at least one of pulmonary gas exchange, barrier thickness or barrier function based on the $^{129}$Xe MRI RBC image.

The methods may optionally include also generating the RBC compartment image and obtaining at least one dissolved phase $^{129}$Xe MRI barrier image signal data of the gas exchange region of the lung and generating a barrier image. The assessing step may include displaying the obtained RBC and barrier images concurrently. The assessing step may include electronically or visually comparing the obtained $^{129}$Xe RBC and barrier images to detect dissolved phase $^{129}$Xe MRI signal attenuation in the $^{129}$Xe RBC image. In particular embodiments, the step of obtaining at least one $^{129}$Xe MRI RBC image signal data and the step of obtaining $^{129}$Xe MRI barrier image signal data may each include obtaining a plurality of respective images with different RF pulse repetition times (TR) of between about 0-60 ms to define signal replenishment on a pixel by pixel basis.

The $^{129}$Xe dissolved phase image signal data may be obtained using a radial imaging sequence and/or a spin-echo imaging sequence.

The obtained $^{129}$Xe MRI RBC (and barrier) image may be generated based on a one-point Dixon mathematical evaluation of MRI dissolved phase $^{129}$Xe signal data comprising both RBC signal data and barrier signal data to thereby differentiate the signal data.

The method may further include obtaining gas-phase $^{129}$Xe MRI image signal data of the patient. Also, the method may optionally include electronically generating a field map of spatially varying field shifts corresponding to magnetic field inhomogeneity associated with an MRI scanner used to generate the obtained gas-phase $^{129}$Xe image signal data; and electronically correcting signal data associated with dissolved phase $^{129}$Xe MRI RBC and barrier images using the field-map of field shifts.

Still other embodiments are directed to methods of assessing pulmonary gas exchange and/or thickening or function of the blood-gas barrier. The methods include: (a) obtaining dissolved phase hyperpolarized $^{129}$Xe NMR spectra having peaks (at about 211 ppm, which for a 2 T system is 5 kHz)) associated with red blood cells (RBC); (b) obtaining dissolved phase hyperpolarized $^{129}$Xe MRI spectra having peaks (at about 197 ppm, (which for a 2 T system the shift is at about 4.66k kHz) associated with a blood-gas barrier; and (c) evaluating a lung based the dissolved phase $^{129}$Xe RBC and barrier spectra peaks.

The spectroscopy method may also include obtaining gas-phase $^{129}$Xe spectra at 0 ppm and comparing the magnitude, height and/or size of peaks in the gas-phase spectra with the dissolved phase spectra to assess pulmonary gas exchange, interstitial lung disease or injury or efficacy of a treatment therefor. Interstitial lung injury or disease may be associated with reduced RBC peak size or height relative to barrier peak size or height. The obtained dissolved phase NMR spectra can be generated using short excitation pulse repetition times (TR) between about 10-200 ms.

Yet other embodiments are directed to methods of generating a three-dimensional $^{129}$Xe MRI image of a lung. The methods include generating a three-dimensional image of a blood-gas barrier of a lung using dissolved phase $^{129}$Xe MRI image signal replenishment data to define barrier thickness and/or impaired barrier function. The method may further include employing radial projection encoding with phase-sensitive image reconstruction to generate the three-dimensional image. A ratio image may also be generated using ratios of barrier and RBC image signal data. The ratio image may be used to illustrate and/or visualize signal attenuation.

In some embodiments, the generating step includes acquiring a plurality of dissolved phase $^{129}$Xe images at multiple repetition times to determine barrier thickness and $^{129}$Xe diffusion. The method may include generating sufficient dissolved phase RBC and barrier image data to curve fit signal replenishment on a pixel-by-pixel basis.

In particular embodiments, the generating the image step includes electronically evaluating signal data using a one-point Dixon evaluation of MRI dissolved phase $^{129}$Xe dissolved phase signal data comprising both RBC signal data and barrier signal data.

Still other embodiments are directed to MRI scanner systems. The MRI scanner systems include: (a) an MRI scanner; and (b) an MRI receiver with a plurality of channels in communication with the MRI scanner, including a first channel configured to receive $^{129}$Xe RBC image data and a second channel configured to receive $^{129}$Xe barrier image data. The MRI scanner is configured to programmatically set the MRI scanner frequency and phase to a $^{129}$Xe dissolved phase imaging mode whereby the scanner frequency and phase is electronically adjusted for xenon alveolar-capillary transfer imaging.

In some embodiments, the first channel receiver phase can be set such that a RBC resonance (such as 211 ppm) corresponds to a real channel and the second channel receiver phase can be set such that a barrier resonance (such as 197 ppm) lags about 90 degrees behind in a negative imaginary channel. Alternatively, the RBC channel can be at +90 degrees (imaginary) and the barrier channel can be at 0 degrees (real).

The MRI scanner may include a scanning sequence that automatically switches the MRI scanner frequency from $^{129}$Xe gas to dissolved phase, then back to $^{129}$Xe gas phase to thereby acquire portions of gas and dissolved image data sets in an interleaved manner. The MRI scanner may be configured to provide a first $^{129}$Xe MRI RBC image of the lung and a second corresponding $^{129}$Xe MRI barrier image of the lung and electronically display the two images substantially concurrently side by side.

Still other embodiments are directed to computer program products for generating $^{129}$Xe MRI images of capillary beds in lungs. The products include computer readable storage medium having computer readable program code embodied therein. The computer readable program code includes computer readable program code configured to obtain a dissolved phase MRI signal of $^{129}$Xe associated with red blood cells in a lung, wherein signal attenuation in the image is associated with reduced alveolar capillary transfer capacity. The program product may also or alternatively include: (a) computer readable program code configured to obtain a dissolved phase MRI signal of $^{129}$Xe associated with a alveolar-capillary barrier in the lung; and (b) computer readable program code configured to obtain an MRI signal of $^{129}$Xe in an air space of the lung.

Although described herein with respect to method aspects of the present invention, it will be understood that the present invention may also be embodied as systems and computer program products.

Other systems, methods, and/or computer program products according to embodiments of the invention will be or become apparent to one with skill in the art upon review of the following drawings and detailed description. It is intended that all such additional systems, methods, and/or computer program products be included within this description, be within the scope of the present invention, and be protected by the accompanying claims.

BRIEF DESCRIPTION OF THE DRAWINGS

Other features of the present invention will be more readily understood from the following detailed description of exemplary embodiments thereof when read in conjunction with the accompanying drawings, in which:

FIGS. 2A-2C are digital images of $^{129}$Xe in an airspace, barrier and RBC of a "sham" animal.

FIGS. 2D-2F are corresponding digital $^{129}$Xe images of an injured animal presenting with left lung fibrosis 11 days post-instillation of bleomycin.

FIG. 3A is a specimen of a control left lung from a right-lung instilled animal. FIG. 3B is a specimen of a damage left lung from a bleomycin-instilled animal.

FIGS. 5A and 5C are dynamic spectroscopy graphs of delay times (ms) versus chemical shift (ppm). FIG. 5A is a graph of dynamic spectra of a control animal and FIG. 5B is a graph of dynamic spectra of an injured animal (rat).

FIGS. 5B and 5D are graphs of signal replenishment, signal integral (arbitrary) versus pulse repetition time (TR)

for the barrier and blood compartments. FIG. 5B corresponds to the control animal and FIG. 5D corresponds to the injured animal (rat).

FIG. 10A is a conventional 3-D projection k-space trajectory.

FIG. 10B is an efficient 3-D trajectory using 30% fewer radial projections than the conventional model, covering k-space with 9329 frames for a 64×64×16 image, according to embodiments of the present invention.

FIGS. 11A-11B are phase-sensitive $^{129}$Xe ventilation (airspace) digital images of a lung. FIG. 11A is a real channel image. FIG. 11B is a imaginary channel image.

FIG. 11C is a phase map generated from the airspace image of data from FIGS. 11A and 11B. The phase variation is due to $B_o$ inhomogeneity.

FIGS. 12A and 12B are graphs of phases of 211 ppm (RBC) and 197 ppm (barrier) resonances. FIG. 12A illustrates the "assumed" phases based on the respective channel allocation (imaginary and real) of the receiver according to embodiments of the present invention. FIG. 12B illustrates "correctable" local misalignment of signal phases due to phase shifts caused by $B_o$ variation according to embodiments of the present invention.

FIG. 13A is a screen printout of barrier images of a healthy rat with different pulse repetition times (TR, 10, 15, 25 and 50) according to embodiments of the present invention.

FIG. 13B is a screen printout of RBC images of a healthy rat with different pulse repetition times (TR, 10, 15, 25 and 50) corresponding to the barrier images in FIG. 13A according to embodiments of the present invention.

DETAILED DESCRIPTION OF EMBODIMENTS OF THE INVENTION

Figure 1A:
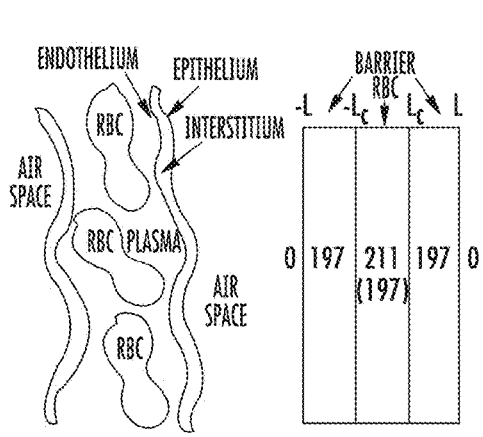
FIG. 1A is a one-dimensional model of gas transfer and signal replenishment in the barrier tissue and RBCs using a simplified depiction of the alveolar capillary unit and corresponding $^{129}$Xe NMR resonance frequencies in air space, barrier, and RBCs.

While the invention may be made in modified and alternative forms, specific embodiments thereof are shown by way of example in the drawings and will be described in detail. It should be understood, however, that there is no intent to limit the invention to the particular forms disclosed, but on the contrary, the invention is to cover all modifications, equivalents, and alternatives falling within the spirit and scope of the invention. Like reference numbers signify like elements throughout the description of the figures.

In the figures, the thickness of certain lines, layers, components, elements or features may be exaggerated for clarity. Broken lines illustrate optional features or operations unless specified otherwise. The sequence of operations (or steps) is not limited to the order presented in the claims or figures unless specifically indicated otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The term "MRI scanner" refers to a magnetic resonance imaging and/or NMR spectroscopy system. As is well known, the MRI scanners include a low field strength magnet (typically between about 0.1 T to about 0.5 T), a medium field strength magnet, or a high-field strength super-conducting magnet, an RF pulse excitation system, and a gradient field system. MRI scanners are well known to those of skill in the art. Examples of commercially available clinical MRI scanners include, for example, those provided by General Electric Medical Systems, Siemens, Philips, Varian, Bruker, Marconi, Hitachi and Toshiba. The MRI systems can be any suitable magnetic field strength, such as, for example, about 1.5 T, and may be higher field systems of between about 2.0 T-10.0 T.

The term "high-field strength" refers to magnetic field strengths above 1.0 T, typically above 1.5 T, such as 2.0 T. However, the present invention is not limited to these field strengths and may suitable for use with higher field strength magnets, such as, for example, 3 T-10 T, or even greater.

The term "hyperpolarized" $^{129}$Xe refers to $^{129}$Xe that has increased polarization over natural or equilibrium levels. As is known by those of skill in the art, hyperpolarization can be induced by spin-exchange with an optically pumped alkali-metal vapor or alternatively by metastability exchange. See Albert et al., U.S. Pat. No. 5,545,396; and Cates et al, U.S. Pat. No. 5,642,625 and U.S. Pat. No. 5,809,801. These references are hereby incorporated by reference as if recited in full herein. One polarizer that is suitable for generating the hyperpolarized $^{129}$Xe is the IGI-9600® polarizer (Inert Gas Imaging) made by Magnetic Imaging Technologies, Durham, N.C. Thus, as used herein, the terms "hyperpolarize", "polarize", and the like mean to artificially enhance the polarization of certain noble gas nuclei over the natural or equilibrium levels.

The term "automatically" means that the operation can be substantially, and typically entirely, carried out without human or manual input, and is typically programmatically directed or carried out. The term "electronically" includes both wireless and wired connections between components. The term "programmatically" means under the direction of a computer program that communicates with electronic circuits and other hardware and/or software.

The term "3-D image" refers to visualization in 2-D what appear to be 3-D images using volume data that can represent features with different visual characteristics such as with differing intensity, opacity, color, texture and the like. For example, the 3-D image of the lung can be generated to illustrate differences in barrier thickness using color or opacity differences over the image volume. Thus, the term "3-D" in relation to images does not require actual 3-D viewability (such as with 3-D glasses), just a 3-D appearance, typically on a display. The 3-D images comprise multiple 2D slices. The 3-D images can be volume renderings well known to those of skill in the art and/or a series of 2-D slices, which can be visually paged through.

Embodiments of the invention may be particularly suitable for use with human patients but may also be used with any animal or other mammalian subject.

The present invention may be embodied as systems, methods, and/or computer program products. Accordingly, the present invention may be embodied in hardware and/or in software (including firmware, resident software, microcode, etc.). Furthermore, the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium, upon which the program is printed, as the program can be electronically captured, via, for instance, optical scanning of the paper or other medium, then compiled, interpreted, or otherwise processed in a suitable manner, if necessary, and then stored in a computer memory. Furthermore, the user's computer, the remote computer, or both, may be integrated into or communicate with other systems, such as MRI scanner systems.

Generally stated, embodiments of the present invention are directed to novel methods of obtaining MRI or NMR signal data of dissolved phase (hyperpolarized) $^{129}$Xe in compartments of the lung associated with gas exchange, including the blood-gas barrier (also known as the alveolar-capillary barrier or "barrier") and/or RBCs.

The present invention can be used to evaluate, qualitatively or quantitatively, a number of lung disorders, conditions, injuries, disease states, disease and the progression or regression thereof. For example, in some embodiments, $^{129}$Xe MRI imaging can show the effects of a thickened blood gas barrier at a single repetition time (TR), which effectively sets a threshold for barrier thickness. For example at TR=50 ms, a barrier greater than 5 µm will appear dark on the RBC image, while a barrier less than 5 µm will appear bright. As will be discussed further below, multiple different repetition times (TR) may also be used, such as, for example, TR between 10-60 ms.

Embodiments of the invention provide clinical evaluation tools and/or research tools that are sensitive to blood gas barrier changes. For example, some embodiments of the invention can be used to differentiate uncertain aetiology of breathlessness or shortness of breath (or other breathing impairments) such as to identify respiratory origin, to determine the adequacy of the alveolar-capillary unit, system or function, and to monitor therapeutic efficacy of treatments on those conditions. In other embodiments, the biophysical or biofunctional reaction to drugs can be assessed during drug discovery programs and/or clinical trials (animal and/or human) and the like to help establish the clinical efficacy and/or negative side effect(s) of the proposed drug.

Still other examples of conditions that may be detected or evaluated using some embodiments of the invention include: (a) detection of alveolitis (inflammation in the alveoli, which inflammation may be a side effect of new drug therapies (the methods may be used to screen new compounds to see whether they cause inflammation)); (b) detection of edema (fluid leakage into the alveoli); (c) detection of pneumonia (infection in the alveoli); (d) detection of fibrosis (increased collagen deposition in the blood-gas barrier (fibrosis can be a complication of radiation therapy of the lung)); and (e) evaluation of drug efficacy for decreased or increased blood gas barrier thickness.

While embodiments of the invention may be particularly suitable for evaluating interstitial lung diseases, the techniques can also be applied to other areas. For example, some methods can be configured to detect emphysema—a decrease in gas exchange surface area (less tissue). In this analysis, a reduction in barrier signal as well as RBC signal (sin ce both tissue and RBC capillary are destroyed) would be expected for this disease state. Also, some methods may be able to detect a pulmonary embolism. That is, depending on the location of the blockage, for example, a blockage upstream from capillaries may impact whether the remaining blood stays in the capillaries or is drained. If the blood drains, then a major reduction in RBC signal would result. If it stays in the capillaries, but just is not flowing, then the xenon alveolar-capillary transfer methods would likely be unaffected. Also, the methods may distinguish the degree of emphysema vs. fibrosis.

In certain embodiments, operations of the invention can be carried out using hyperpolarized $^{129}$Xe to evaluate respiratory and/or pulmonary disorders. For example, $^{129}$Xe image data and/or NMR spectroscopic signals of $^{129}$Xe can be used to obtain data regarding pulmonary physiology and/or function in order to assess, diagnose, or monitor one or more of: a potential bioreaction to a transplant, such as transplant rejection (of transplanted organs in the body, whether lung, heart, liver, kidney, or some other organ of interest), environmental lung disorders, pneumonitis/fibrosis, pulmonary hypertension, pulmonary inflammation such as interstitial and/or alveolar inflammation, interstitial lung diseases or disorders, pulmonary and/or alveolar edema with or without alveolar hemorrhage, pulmonary emboli, drug-induced pulmonary disorders, diffuse lung disorders, chronic obstructive pulmonary disease, pneumoconiosis, tuberculosis, pleural thickening, cystic fibrosis, pneumothorax, non-cardiogenic pulmonary edema, angioneurotic edema, angioedema, type I alveolar epithelial cell necrosis, hyaline membrane formation, diffuse alveolar damage such as proliferation of atypical type II pneumocytes, interstitial fibrosis, interstitial and/or alveolar infiltrates, alveolar septal edema, chronic pneumonitis/fibrosis, bronchospasm, bronchialitis obliterans, alveolar hemorrhage, aspiration pneumonia, hypercapnic respiratory failure, alveolitis/fibrosis syndrome, systemic lupus erythematosus, chronic eosinophilic pneumonia, acute respiratory distress syndrome, and the like.

The lung can be a target of drug toxicity. It is known, for example, that many medications, including chemotherapeutic drugs, anti-inflammatory drugs, anti-microbial agents, cardiac drugs and anticonvulsants can cause lung injury, including lung toxicity, that can be progressive and result in respiratory failure. See *Diffuse Lung Disorders: A Comprehensive Clinical-Radiological Overview*, Ch. 19, *Drug-Induced Pulmonary Disorders*, (Springer-Verlag London Ltd, 1999), the contents of which are hereby incorporated by reference as if recited in full herein. Examples of drug-induced lung disorders that may be able to be evaluated according to embodiments of the present invention include, but are not limited to: pneumonitis/fibrosis, interstitial lung disease, interstitial or pulmonary honeycombing and/or fibrosis, hypersensitivity lung disease, non-cardiogenic pulmonary edema, systemic lupus erythematosus, bronchiolitis obliterans, pulmonary-renal syndrome, bronchospasm, alveolar hypoventilation, cancer chemotherapy-induced lung disease, pulmonary nodules, acute chest pain syndrome, pulmonary infiltrates, pleural effusion and interstitial infiltrates, angioedema, cellular atypia, diffuse reticular or reticulonodular infiltrates, bilateral interstitial infiltrates, reduced diffusing capacity, parenchymal damage with alveolar epithelial hyperplasia and fibrosis and/or atypia, early onset pulmonary fibrosis, late-onset pulmonary fibrosis, and subacute interstitial lung disease.

Some of the above-conditions have been known to occur with specific drugs, such as mitomycin and bleomycin, and, in certain embodiments of the invention, MRI-data and/or NMR-derived data of hyperpolarized $^{129}$Xe can be used while the patient is being treated with the potentially problematic drug to allow earlier intervention or alternate treatments should the lung exhibit a drug-induced disorder.

In some situations, patients can experience the onset of lung injury at the early onset of treatment with a therapeutic agent or in a certain environment. However, presentation of the injury can be delayed. In certain situations, the symptoms can present acutely with rapid deterioration. In either case, early identification of the problem can allow earlier intervention.

Effective pulmonary gas exchange relies on the free diffusion of gases across the thin tissue barrier separating air space from the capillary RBCs. Pulmonary pathologies, such as inflammation, fibrosis, and edema, which cause an increased blood-gas barrier thickness, impair the efficiency of this exchange. However, definitive assessment of such gas-exchange abnormalities is challenging because no known methods directly image the gas transfer process. Embodiments of the instant invention can exploit the solubility and chemical shift of $^{129}$Xe, the magnetic resonance (MR) signal of which has been enhanced by $10^5$ via hyperpolarization, to differentially image its transfer from the air spaces into the tissue barrier spaces and RBCs in the gas exchange regions of the lung. The novel MR imaging (or NMR spectroscopy) methods for evaluating $^{129}$Xe alveolar-capillary transfer are sensitive to changes in blood-gas barrier thickness of approximately 5 μm. The imaging methods have allowed successful separation of tissue barrier and RBC images of a rat model of pulmonary fibrosis where $^{129}$Xe replenishment of the red blood cells is severely impaired in regions of lung injury.

While not wishing to be bound to any particular theory, it is presently believed that three properties of $^{129}$Xe make it well suited for magnetic resonance imaging (MRI) of the pulmonary gas exchange process and/or NMR spectroscopy of barrier and RBC compartments that can be used to evaluate the gas exchange process or health status of the lung(s). First, xenon is soluble in the pulmonary tissue barrier and RBC compartments. Second, $^{129}$Xe resonates at three distinct frequencies in the air space, tissue barrier, and RBC compartments. Third, the $^{129}$Xe magnetic resonance signals can be enhanced by a factor of ~$10^5$ making it possible to image this gas with a resolution approaching proton-MRI.

When $^{129}$Xe is inhaled into the lung and enters into the alveolar air-spaces, a small fraction is absorbed into the moist epithelial surface. The atoms diffuse across the tissue barrier and their concentration in the RBCs in the capillary beds equilibrates with that in the air-space. The atoms continue to exchange among all three compartments before those in the RBCs and plasma are carried away in the pulmonary circulation. When $^{129}$Xe dissolves, its NMR frequency shifts dramatically from the free gas frequency. $^{129}$Xe in the alveolar epithelium, interstitium, capillary endothelium, and plasma resonate at a frequency that is shifted 197 parts per million (ppm) (4.64 kHz in a 2 Tesla field) from the gas reference frequency at 0 ppm (9). Since these tissues lie between the air space and RBCs, this group of 197 ppm shifted signals can be referred to as the "barrier" resonance. Once $^{129}$Xe leaves the barrier and reaches the red blood cells its resonant frequency shifts yet again to 211 ppm from the gas frequency (10) and this can be referred to as the "RBC" resonance. Collectively the 197 ppm and 211 ppm signals are referred to as the "dissolved phase," consistent with prior literature.

| B0 | gas (MHz) | 197 ppm (Hz) | 211 ppm (Hz) |
| --- | --- | --- | --- |
| 1.5T | 17.73 | 3493 | 3741 |
| 3T | 35.46 | 6986 | 7482 |
| 7T | 82.74 | 16300 | 17458 |

In the past, it is believed that Ruppert et al. first used dynamic spectroscopy to measure the replenishment rate of $^{129}$Xe signal in the barrier and RBC compartments of the lung after magnetization therein was destroyed by a frequency-selective radio frequency (rf) pulse (11). Unlike conventional proton MRI, once the hyperpolarized noble gas atoms are depolarized by the rf pulse, their thermal repolarization by the static magnetic field is negligible and thus, as probes, become silent. The 197 ppm and 211 ppm signals are only replenished as fresh gas phase $^{129}$Xe magnetization diffuses back into the dissolved phase compartments on a time scale of ~30-40 ms in a healthy lung. Mansson and co-workers used this spectroscopic technique to show that the time constants for the barrier and RBC signal replenishment were significantly increased in rat lungs that had been exposed to the inflammatory agent, lipo-polysaccharide (8). Recently, Abdeen and co-workers have used similar methods to show reduce gas transfer in cases of lung inflammation induced by instillation of *Stachybotrys chartarum* (12).

The present invention recognizes that one aspect of $^{129}$Xe gas exchange that is sensitive to blood-gas barrier health status, however, is the time it takes $^{129}$Xe to reach the red blood cells. To exhibit the 211 ppm blood resonance, $^{129}$Xe must first traverse the 197 ppm barrier separating RBCs from the air space, thus delaying the RBC signal appearance. The time-constant for $^{129}$Xe diffusion across this barrier can be estimated as $\tau \approx \Delta L_{db}^2/2D$, where $\Delta L_{db}$ is the barrier thickness and D is the Xe diffusion coefficient. In a healthy subject (rat/human) with a blood-gas barrier of thickness ~1 µm, and D≈0.33×10$^{-5}$ cm$^2$s$^{-1}$ (13), $^{129}$Xe transit takes only 1.5 ms. Such a delay is short compared to MR imaging repetition rates (TR) of 5-10 ms and therefore is difficult to detect. However, because diffusing time scales as the square of the barrier size, a thickness increase to 5 µm would delay the appearance of the 211 ppm resonance by about 40 ms, a timescale more easily probed. It is believed that such a striking delay of the RBC replenishment has not been observed in spectroscopy studies to date. This may be because pathology-induced diffusion barrier thickening is not uniform across the entire lung in a disease model. Thus, the global RBC signal replenishment observed by spectroscopy is dominated by the healthy lung regions where $^{129}$Xe-blood transfer remains rapid. To observe the RBC (211 ppm) signal delay associated with regional thickening of the diffusion barrier, imaging of the $^{129}$Xe RBC bound phase can be used.

Imaging $^{129}$Xe dissolved in lung tissues is significantly more challenging than imaging $^{129}$Xe in the airspaces. First, the lung tissue volume is only about 10% that of the airspace volume (14) and further, the solubility of Xe in lung tissues is only ~10% (15, 16), leading to 197 ppm and 211 ppm signals that are no more than 1% of the airspace signal at any given instant. Second, once $^{129}$Xe is dissolved in lung tissue, the susceptibility-induced transverse relaxation time $T_2^*$ is reduced from 20 ms to ~2 ms. However, understanding this behavior, imaging methods can provide for this relaxation time with sub-millisecond echo times and high bandwidth. Third, $^{129}$Xe has the ability to separately image in the three different frequency compartments. Such an ability can, for example, elucidate the exchange dynamics, provide better sensitivity as to function, barrier thickness, disease states, drug therapies and the like.

It is believed that, to date, only Swanson and co-workers have succeeded in direct imaging of $^{129}$Xe in the dissolved compartments of the thorax of the lung by using chemical shift imaging (17). Their use of 30° flip angles and a repetition time of 428 ms ensured that $^{129}$Xe signal was grossly localized to the thorax, but not specifically from the gas exchange regions of the lung. An alternate prior art imaging approach that retains higher spatial resolution while indirectly probing the gas exchange process is called Xenon polarization Transfer Contrast (XTC). This method uses the attenuation of airspace $^{129}$Xe signal after RF irradiation of the dissolved phase $^{129}$Xe frequencies to indirectly map $^{129}$Xe gas exchange between airspace and dissolved phase (18). XTC has been shown to be sensitive to tissue density increases due to atelectasis, for example (13), but it is believed that this methodology cannot, at least presently, distinguish $^{129}$Xe signal originating from the barrier and RBC compartments.

Embodiments of the invention can provide methods for efficient differential imaging of $^{129}$Xe in the airspace, barrier, and RBC compartments of the lung with 16-fold higher resolution than was previously attained (17). Furthermore, as contemplated by some embodiments, directing the imaging to the gas exchange regions of the lung, and separating out barrier and RBC images, can provide specific sensitivity to pulmonary gas exchange. As will be discussed further below, a successful differentiation of RBC and barrier images was obtained using a rat model of pulmonary fibrosis in which, at regions of diffusion barrier thickening, the RBC image is depleted while the barrier image continues to substantially if not identically match the airspace image. According to some embodiments of the present invention, $^{129}$Xe imaging methods that evaluate the blood-gas barrier using image data from one or more of $^{129}$Xe MRI barrier and/or RBC images can be referred to as Xenon Alveolar Capillary Transfer imaging or "XACT".

To generally understand $^{129}$Xe signal dynamics in the airspace, barrier and RBC compartments, a simple one-dimensional model of gas diffusion in the lung can be used. While more complex three-dimensional models merit consideration (8), a simple model can facilitate an understanding of the primary factors governing dissolved $^{129}$Xe signal replenishment, particularly the delayed return of $^{129}$Xe-RBC signal, an aspect overlooked in the hyperpolarized $^{129}$Xe studies performed to date. FIG. 1A shows a simple one-dimensional model of gas transfer and signal replenishment in the barrier tissue and RBCs. FIG. 1A depicts an air space, pulmonary endothelium, interstitial space, capillary endothelium, plasma, and RBCs. The whole barrier/RBC block can be defined as extending from $-L \leq x \leq L$, while the RBC component extends only across the capillary range $-L_c \leq x \leq L_c$ with $L_c < L$. The thickness of the diffusion barrier is then $\Delta L_{db} = L - L_c$.

Figure 1B:
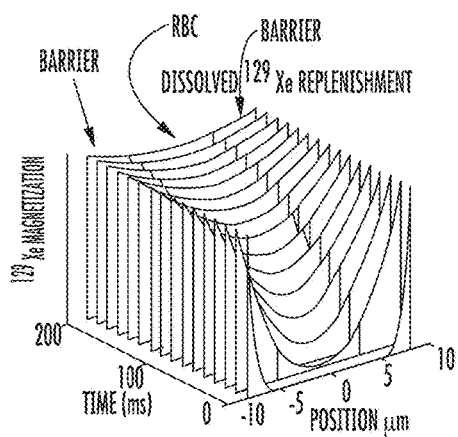
FIG. 1B is a three-dimensional graph of position (μm), time (ms) and $^{129}$Xe magnetization of dissolved $^{129}$Xe replenishment.
Figure 1C:
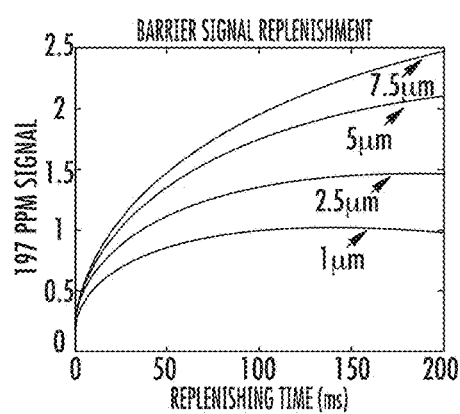
FIG. 1C is a graph of barrier signal (197 ppm) replenishment versus time (ms) for barrier thicknesses $\Delta L_{db}$ ranging from 1 μm to 7.5 μm.
Figure 1D:
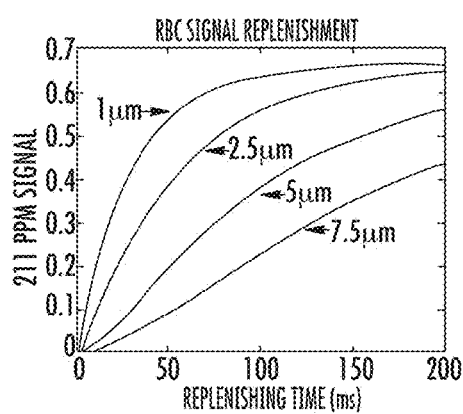
FIG. 1D is a graph of RBC signal (211 ppm) replenishment versus time (ms) for the same range of barrier thickness as in FIG. 1C and constant $L_c$=4 μm.

FIG. 1B illustrates replenishing of the $^{129}$Xe magnetization profile across the entire tissue block including barrier and RBC. FIG. 1C illustrates replenishing of the barrier signal (197 ppm) for barrier thicknesses $\Delta L_{db}$ ranging from 1 µm to 7.5 µm, assuming $D_{Xe}$=0.33×10$^{-5}$ cm$^2$s$^{-1}$. FIG. 1D illustrates replenishing of the RBC signal (211 ppm) for the same range of barrier thickness and constant $L_c$=4 µm. As barrier thickness increases, return of the RBC signal appearance is delayed.

The replenishment of the dissolved $^{129}$Xe magnetization can be calculated after it is destroyed by a frequency-selective 90° rf pulse. It is assumed that the $^{129}$Xe magnetization in the airspaces (0 ppm) is unaffected by the rf pulse Immediately after the rf pulse, $^{129}$Xe diffusion begins to re-equilibrate the gaseous and dissolved $^{129}$Xe magnetizations. A rapidly converging series solution to this type of symmetric diffusion problem is provided by Crank (19). The dissolved $^{129}$Xe magnetization profile after replenishing time t, can be expressed by Equation (1):

$$M_{diss}(x, t) = \lambda M_{air} \sum_{n=0}^{\infty} (-1)^n \left( \text{erfc}\left(\frac{(2n+1)L+x}{2\sqrt{Dt}}\right) + \text{erfc}\left(\frac{(2n+1)L-x}{2\sqrt{Dt}}\right)\right) \quad (1)$$

where $\lambda$ is the solubility of Xe in tissue and $M_{air}$, is the $^{129}$Xe magnetization in the air space. Here erfc(x)=1−erf(x)

is the error function complement with the properties erfc(0)=1, erfc(∞)=0. Several simplifying assumptions have been made to preserve the clarity of the discussion. First, the Xe solubility and diffusion coefficient are the same throughout the dissolved phase. Second, because the primary interest is in signal replenishment on short time scales compared to capillary transit time (t<300 ms), the effects of blood flow can be ignored. Third, the short-time interest period allows the $^{129}$Xe longitudinal relaxation to be ignored since the shortest known $T_1$ of $^{129}$Xe in biological fluids is 4 seconds in venous blood (20) and $^{129}$Xe $T_1$ is >100 s in aqueous environments (21). FIG. 1B depicts the dissolved $^{129}$Xe magnetization replenishment profile. The $^{129}$Xe magnetization fills the dissolved phase from the edges (barrier), with the central portions (RBC) of the capillary regaining magnetization last. After sufficient equilibration time, $Dt/L^2 \gg 1$, a homogeneous $^{129}$Xe magnetization profile again exists across the entire tissue block.

The replenishment of $^{129}$Xe signal from the barrier and RBC compartments can be determined by integrating the $^{129}$Xe magnetization profile over the regions bounding the 197 ppm and 211 ppm resonances. The 211 ppm RBC resonance is most straightforward to calculate as it results directly from the interaction of $^{129}$Xe with red blood cells. There is some controversy between available in vitro (9, 20, 22) and in vivo data (17) as to whether the 211 ppm peak is purely due to $^{129}$Xe bound to RBCs or whether it results from rapid $^{129}$Xe exchange between plasma and RBCs. However, these issues do not impact the conclusion that the 211 ppm signal is incontrovertibly associated with $^{129}$Xe-RBC interaction, but is noted for completeness. Also, like Mansson et al., it is assumed that $^{129}$Xe in plasma retains its 197 ppm signal and thus the 211 ppm signal results only from $^{129}$Xe interacting with the hematocrit, the fraction of blood composed of RBCs (8). Therefore, it is believed that 211 ppm signal replenishment is thus obtained according to Equation (2) by integrating the $^{129}$Xe magnetization over the capillary dimension $L_c$ and scaling by hematocrit fraction Hct which is 0.45-0.50 in healthy rats (23).

$$S_{211}(t) = G_{MR} \cdot Hct \int_{-L_c}^{L_c} M_{diss}(x, t) dx \qquad (2)$$

$G_{MR}$ is a scaling factor representing the MRI signal chain. The 197 ppm signal can thus be expressed along the lines of Equation (3), as the entire dissolved phase integral minus the 211 ppm signal.

$$S_{197}(t) = G_{MR} \int_{-L}^{L} M_{diss}(x, t) dx - S_{211}(t) \qquad (3)$$

The solution to the RBC signal, normalized by the airspace signal $S_0$ to absorb all the MR signal chain scaling constants, can be expressed by Equation (4):

$$\frac{S_{211}(t)}{S_0} = \frac{4\lambda Hct \sqrt{Dt}}{L_A} \qquad (4)$$

$$\sum_{n=0}^{\infty} (-1)^n \left( ierfc\left(\frac{(2n+1)L - L_c}{2\sqrt{Dt}}\right) - ierfc\left(\frac{(2n+1)L + L_c}{2\sqrt{Dt}}\right) \right)$$

where the airspace signal $S_0 = M_{air} L_A$, and $L_A$ is the linear dimension of an alveolus in this simple one-dimensional model. Here, ierfc(x) is the integral of the error function complement with the properties ierfc(0)=$1/\sqrt{\pi}$ and ierfc(∞)=0. One aspect of equation (4) is that because $L_c < L$, the replenishment of $S_{211}$ can be delayed, depending on the thickness $\Delta L_{db}$ of the diffusion barrier separating the airspace and the blood cells. For completeness, the integrated intensity of the 197 ppm barrier resonance can be expressed by Equation (5):

$$\frac{S_{197}(t)}{S_0} = \qquad (5)$$

$$\left( \frac{4\lambda\sqrt{Dt}}{L_A} \sum_{n=0}^{\infty} (-1)^n \left( ierfc\left(\frac{(2n+1)L - L}{2\sqrt{Dt}}\right) - ierfc\left(\frac{(2n+1)L + L}{2\sqrt{Dt}}\right) \right) \right) - \frac{S_{211}(t)}{S_0}$$

Note that $S_{197}$ will begin replenishing immediately after the RF pulse, as fresh $^{129}$Xe from the air space diffuses in with initial signal growth scaling as $\sqrt{Dt}$ and surface-to-volume ratio ($1/L_A$) as discussed by Butler (24). FIG. 1C and FIG. 1D show the calculated replenishment of the barrier and RBC signals for a range of barrier thicknesses 1 µm≤$\Delta L_{db}$≤7.5 µm with $L_c$ fixed at 4 µm, half the diameter of a red blood cell. By way of example, a Xe diffusion coefficient of $0.33 \times 10^{-5}$ cm$^2$s$^{-1}$ can be assumed (13) as can a hematocrit fraction of 0.5. The delayed replenishment of the RBC resonance when the diffusion barrier $\Delta L_{db}$ has thickened beyond 1 µm is readily apparent in FIG. 1D. Note that the expected reduction in RBC signal amplitude associated with barrier thickening is much greater than the corresponding increase in barrier signal. For example, at a replenishment time of 50 ms, the RBC signal is reduced 640% for the 7.5 µm barrier vs the 1 µm barrier, while the barrier signal is increased by 68%.

To generate images of the dissolved $^{129}$Xe compartments, the continuous magnetization replenishment from the gas-phase alveolar reservoir can be exploited. Since dissolved $^{129}$Xe magnetization recovers with about a ~40 ms time constant in healthy lung, we can apply a large angle pulse, typically about a 90° pulse at roughly that repetition rate. The repetition rate effectively sets the replenishment timescale and, thus, the diffusion distance scale that can be probed with imaging. SNR can be extended by ~2 by acquiring image data throughout the breathing cycle. To overcome the exceedingly short $T_2^*$ of dissolved phase $^{129}$Xe (about a 1.7 ms estimate), radial imaging can be used (25, 26).

Embodiments of the invention are directed at ways to discriminate $^{129}$Xe in the airspace, barrier, and RBC compartments so that gas transfer dynamics can be discerned. Previously, $^{129}$Xe frequency discrimination was proposed using chemical shift imaging (CSI) (17). However, for the lung, CSI is unacceptably slow and not amenable to high-resolution imaging on fast time scales. Frequency-selective rapid Fourier imaging is possible when two resonances are present, as was first demonstrated by Dixon for fat and water separation (27). Thus, imaging two resonances can be achieved using a frequency selective pulse that excites both the 197 and 211 ppm resonances, but not the gas phase resonance at 0 ppm. A one-point variant of the Dixon technique can be used to obtain separate images of the 197 ppm and 211 ppm compartments from the real and imaginary components of a single image (28).

Dixon imaging exploits the slight difference in the transverse-plane precession frequency of two resonances to image them at a predicted phase shift. After the frequency selective rf pulse places the 197 ppm and 211 ppm magnetization into the transverse plane, the 211 ppm magnetization will precess 330 Hz faster (at 2 T) than the 197 ppm resonance. This phase evolution can be allowed to occur just long enough for the 211 ppm spins to accumulate 90° of phase relative to the 197 ppm spins. Then the imaging gradients can be turned on to encode the spatial information. The scanner receiver phase is set so that one resonance contributes to the in-phase image and the other to the out-of-phase image. Phase-sensitive imaging allows an image of $^{129}$Xe replenishment in the barrier in one channel and in the RBCs in the other channel to be obtained. A phase evolution period that can be used to achieve a 90° phase difference is $TE_{90°}=\frac{1}{4}\Delta f$ where $\Delta f$ is the frequency difference between the two resonances.

Experimental Overview

All experiments were performed using Fischer 344 rats weighing 170-200 g (Charles River Laboratories, Raleigh, N.C.). Various aspects of the $^{129}$Xe imaging and spectroscopy protocol were initially developed using 35 healthy animals. The final protocol consisting of a high-resolution (0.31×0.31 mm$^2$) ventilation image, a phase-sensitive barrier/RBC replenishment image (1.25×1.25 mm$^2$), and dynamic $^{129}$Xe spectroscopy was used to study 9 animals Seven animals had unilateral fibrosis induced by bleomycin instillation, one healthy control, and one sham instillation. Animals were imaged 5-15 days after bleomycin instillation, when inflammatory and early fibrotic changes would present a thickened diffusion barrier.

The animal protocol was approved by the Institutional Animal Care and Use Committee at Duke University. Interstitial fibrosis was induced by unilateral instillation of bleomycin (29). Rats were anesthetized with 46 mg/kg methohexital (Brevital, Monarch Pharma, Bristol, Tenn.) and perorally intubated with an 18 G catheter (Sherwood Medical, Tullamore, Ireland). A curved PE50 catheter was advanced through the endotracheal tube and manipulated to enter the chosen (left or right) pulmonary main bronchus. While the animal was positioned head-up on a 45° slant board, a solution of bleomycin (Mayne Pharma, Paramus, N.J.) in saline (2.5 units/kg) was slowly instilled over a period of 10 seconds. Because the left lung is significantly smaller than the right, a higher concentration/lower volume of bleomycin was used for left lung instillations. For the left lung, 0.07 ml at 6.8 units/ml was instilled, whereas the right lung received 0.2 ml at 2.5 units/ml bleomycin. Sham instillations were performed similarly using an equivalent volume of saline.

$^{129}$Xe Polarization

Polarization of $^{129}$Xe was accomplished using continuous flow and cryogenic extraction of $^{129}$Xe (30). A mixture of 1% Xe, 10% N$_2$ and 89% $^4$He (Spectra Gases, Alpha, N.J.) flowed at 1-1.5 SLM through the optical cell containing optically pumped Rb vapor at a temperature of 180° C. Spin exchange collisions between the Rb valence electrons and $^{129}$Xe transfer red angular momentum to the $^{129}$Xe nuclei with an estimated time constant of 6 s. Upon exiting the optical cell, hyperpolarized $^{129}$Xe was extracted from the other gases by freezing in a 77 K cold trap located in a 3 kG magnetic field to preserve solid $^{129}$Xe polarization (31). Once a suitable quantity of solid polarized $^{129}$Xe was produced, it was thawed and captured for delivery. A prototype commercial polarizer (IGI.9600.Xe, Magnetic Imaging Technologies, Durham, N.C.) was used to polarize ~500 ml of $^{129}$Xe gas to 8-9% polarization in 45 minutes. After accumulation of $^{129}$Xe was complete, it was thawed and collected in a 1 liter Tedlar bag (Jensen Inert Products, Coral Springs, Fla.) housed in a Plexiglas cylinder. The cylinder was then detached from the polarizer and attached to a hyperpolarized gas compatible ventilator. For all experiments reported here, xenon was enriched to 83% $^{129}$Xe. For spectroscopy studies, about 150 ml of enriched $^{129}$Xe was polarized and diluted with 350 ml of N$_2$.

Animal Preparation—Imaging

Animals were first anesthetized with intraperitoneal (IP) injection of 56 mg/kg ketamine (Ketaset, Wyeth, Madison, N.J.) and 2.8 mg/kg diazepam (Abbott Labs, Chicago, Ill.). During imaging anesthesia was maintained with periodic injection of ketamine and diazepam at ¼ the initial dose. Rats were perorally intubated using a 16-gauge catheter (Sherwood Medical). The rat was ventilated in a prone position at a rate of 60 breaths/min and a tidal volume of 2.0 ml using a constant volume hyperpolarized gas ventilator as described by Chen et al., (32). During $^{129}$Xe imaging, breathing gas was switched from air to a mixture of 75% HP xenon mixed with 25% O$_2$ to achieve a tidal volume of 2 ml. A single breath was characterized by a 300 ms inhalation, 200 ms breath-hold, and a 500 ms passive exhalation. The ventilator triggered the MRI scanner at the end of inspiration for high-resolution airspace imaging during the breath-hold. Airway pressure, temperature, and ECG were monitored continuously and body temperature was controlled by warm air circulating through the bore of the magnet using feedback from a rectal temperature probe.

Imaging and Spectroscopy Hardware

All images and spectra were acquired on a 2.0 T horizontal 30 cm clear bore magnet (Oxford Instruments, Oxford, UK) with shielded gradients (18 G/cm), controlled by a GE EXCITE 11.0 console (GE Healthcare, Milwaukee, Wis.). The 64 MHz rf system was made to operate at the $^{129}$Xe frequency of 23.639 MHz using an up-down converter (Cummings Electronics Labs, North Andover, Mass.). A linear birdcage rf coil (7 cm diameter, 8 cm long) operating at 23.639 MHz was used for imaging An integrated Transmit/Receive switch and 31 dB gain preamplifier (Nova Medical, Wilmington, Mass.) was interfaced between the coil and scanner.

Airspace $^{129}$Xe Imaging Procedure

Airspace $^{129}$Xe images were acquired using a radial encoding sequence that has been described previously (33). Images were acquired without slice selection, 4 cm FOV, 8 kHz bandwidth, and reconstructed on a 128×128 matrix with a Nyquist resolution limit of 0.31×0.31 mm$^2$ in-plane. K-space was filled using 400 radial projections, 10 views per breath, TR=20 ms, thus employing 40 breaths (40 s) to complete the image. For each view n in a breath, a variable flip angle scheme, calculated according to $\alpha_n=\arc\tan(1/\sqrt{10-n})$ (34), was employed to both use the available magnetization most efficiently and to generate images that distinguish the major airways from parenchyma. All imaging and spectroscopy employed a truncated sinc excitation pulse with one central lobe and one side lobe on either side. To avoid contaminating the airspace image with $^{129}$Xe signal from the barrier and RBC compartments, a total pulse length of 1.2 ms with frequency centered on gas-phase $^{129}$Xe (0 ppm) was used.

Dynamic Spectroscopy Procedure

Dynamic spectra measuring $^{129}$Xe replenishment in the entire lung were acquired with repetition time (TR) values ranging from 11 to 200 ms. 90° excitation pulses of 1.05 ms duration centered at 204 ppm were used to simultaneously read and destroy the $^{129}$Xe magnetization in the 197 and 211 ppm compartments. 256 points per spectrum were acquired at a bandwidth of 15 kHz, (32 us dwell time). The bandwidth of the 1.05 ms sin c pulse excited the barrier and RBC resonances with a 90° flip while providing a 0.15° flip to the airspace $^{129}$Xe to provide the 0 ppm reference frequency. Spectra were recorded using TR values of 11, 15, 20, 30, 40, 50, 75, 100, 125, 150, 175, and 200 ms. For each TR value, the maximum number of spectra was acquired during the 200 ms breath-hold and averaged over 5 breaths. The first spectrum of each breath-hold period was discarded, sin ce it resulted from 800 ms of replenishment rather than the specified TR period. The raw data for each spectrum was line broadened (25 Hz), baseline corrected, Fourier transformed and fit using routines written in the MATLAB environment (The MathWorks, Natick, Mass.). Curve fitting of the real and imaginary spectra prior to phase correction allowed extraction of the amplitudes, frequencies, linewidths, and phases of each resonance. This information was used to set the receiver frequency and phase to ensure that, in subsequent barrier/RBC imaging, the imaginary channel contained the $^{129}$Xe-barrier image and the real channel contained the $^{129}$Xe-RBC image.

Barrier/RBC $^{129}$Xe Replenishment Imaging Procedure

Non-slice-selective $^{129}$Xe images of the barrier and RBC compartments were acquired using 2D radial projection encoding with a TR of 50 ms, a 90° flip angle, an FOV of 8 cm, and a grid of 64×64 for a Nyquist resolution limit of 1.25×1.25 mm$^2$. The combination of a 90° flip angle and a TR of 50 ms made the images sensitive to diffusion barrier thickening on the order of 5 µm. A 1.2 ms sin c pulse centered on the 211 ppm blood resonance was used to excite only the 197 and 211 ppm resonances, and not the airspace $^{129}$Xe. This minimum pulse duration yielding no detectable 0 ppm signal was determined using phantoms containing only gas-phase hyperpolarized $^{129}$Xe. An imaging bandwidth of 15 kHz ensured that radial encoding lasted roughly 2 ms, on the same order as $T_2^*$ decay. K-space was overfilled using 2400 frames acquired throughout the ventilation cycle to maximize signal averaging from the barrier/RBC compartments. Thus, the dissolved image used about 120 breaths (2 min) to acquire. To discriminate the 197 and 211 ppm resonance, the echo time was calculated according to $TE_{90}=¼\Delta f$. At 2 Tesla one can calculate $TE_{90}=755$ µs for the 211 ppm RBC and 197 ppm barrier resonances. Empirically, however, the echo time $TE_{90}$ can be determined using whole-lung spectroscopy and an optimal value was found to be closer to 860 µs-940 µs, varying slightly in each animal. The slight discrepancy between calculated and empirical echo times is not fully understood, but may be explained by the long duration of the rf pulse, compartmental exchange of $^{129}$Xe during the rf pulse, or field inhomogeneity over the entire lung. Phase-sensitive images were reconstructed such that the real image displayed $^{129}$Xe in the 211 ppm RBC compartment and the imaginary image contained the 197 ppm barrier image.

Histology

After imaging, rats were sacrificed with a lethal dose of pentobarbital (Nembutal, Abbott Labs, Chicago, Ill.). Lungs were instilled with 10% formalin at 25 cm $H_2O$ for 30 minutes and thereafter stored in 10% formalin. The lungs were processed for conventional histology and stained with H&E stain and Masson's Trichrome for collagen. Slides were evaluated to look for thickening of the alveolar septa, qualitative correspondence of location and extent of the injury with imaging, and to confirm that the contralateral lung was uninjured. A semi-quantitative measure of the fraction of each lung lobe affected by the bleomycin was determined by visual inspection.

Image Analysis

Images of $^{129}$Xe in the airspace, barrier, and RBCs were analyzed using an automated routine written in MATLAB (The MathWorks, Natick, Mass.) to quantify the number of image pixels containing signal. Pixels were considered "on" if they exceeded two times the mean of the background noise. Signal to noise for each image was calculated by dividing the mean value of all the pixels above threshold with mean background signal. The unilaterally induced injury made it fruitful to analyze left and right lungs separately by manually drawing a border between the two lobes of the ventilation image. Because images were two-dimensional, the portion of the right accessory lobe that overlaps with the left lung was unavoidably counted in the left lung. In each lung the ratio of signal-containing pixels in RBC and barrier images (RBC/barrier ratio) was taken as the primary measure of gas transfer efficiency.

Spectroscopy Analysis

The 211 and 197 ppm signal integrals derived from dynamic whole-lung spectroscopy were fit to equations (4) and (5) governing their replenishment. Because the injury was nonuniform and spectroscopy signals originate from the entire lung, any regional delay in RBC signal due to barrier thickening is obscured by the healthy regions of the lung where RBC signal replenishment remains rapid. Thus, the shape of each replenishment curve was qualitatively indistinguishable between healthy and treated animals and curve fitting could not extract independent values for the diffusion coefficient D, and length parameters L, and $L_c$. Instead, D was held fixed at $0.33\times10^{-5}$ cm$^2$s$^{-1}$ and L, $L_c$, and the saturation amplitudes were extracted. However, regions of RBC signal delay did result in an overall reduction in the 211 ppm signal integral relative to the 197 ppm signal. Thus, from the amplitudes of fitted curves, the ratio of RBC/barrier integral could be calculated for each animal and used as a measure of gas transfer efficiency.

FIGS. 2A-2F shows images of $^{129}$Xe in the airspaces, barrier and RBC. FIGS. 2A-2C correspond to a left lung sham-instilled rat (#2) and FIG. 2D-2F correspond to a rat with left lung fibrosis (#5) imaged 11 days post-bleomycin instillation. Most notable is the nearly complete absence of $^{129}$Xe RBC replenishment in the injured lung of the diseased animal (FIG. 2F), whereas barrier replenishment appears closely matched to the airspace image (see barrier images in FIGS. 2B and 2E that closely match the corresponding air space images in FIGS. 2A and 2D).

The absence of signal indicates that $^{129}$Xe does not reach the RBCs on the 50 ms image acquisition time scale, likely resulting from increased diffusion barrier thickness. The matching of barrier image intensity with airspace image intensity was noted in all studies. The mismatching of RBC replenishment with barrier replenishment was a hallmark finding in all injured lungs. Absence of RBC replenishment on the 50 ms imaging time-scale is consistent with the predictions of the simple model and suggests thickening of the diffusion bather beyond its normal thickness of 1 µm to greater than 5 µm (assuming D=$0.33\times10^5$ cm$^2$s$^{-1}$). Note also that the volume of the left fibrotic lung is reduced on the airspace image (FIG. 2D), while the right lung exhibits compensatory hyperinflation. This reduction in volume of the injured lung was noted in all 7 bleomycin treated animals.

Figures 3A, 3B:
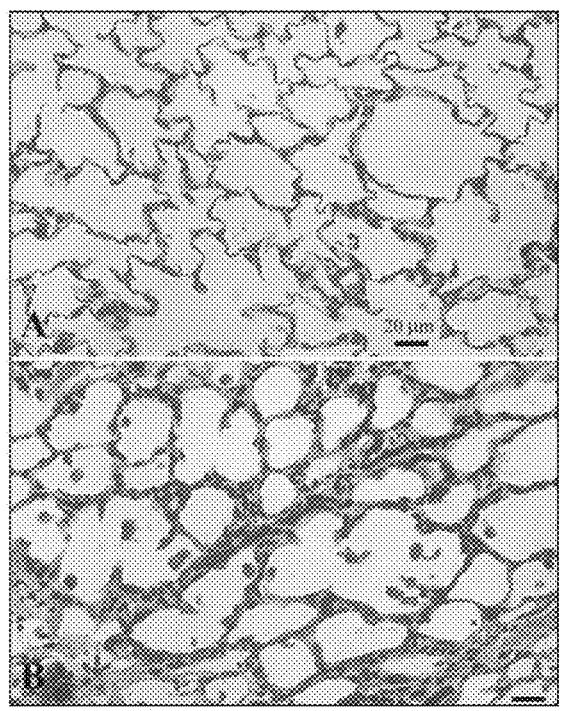
FIGS. 3A and 3B are Hematoxylin Eosin (H&E) stained histology.

H&E stained sections from a control left lung of rat #8 (FIG. 3A) and the bleomycin instilled left lung of rat #5 (FIG. 3B). Thickened alveolar septa are clearly visible in the treated lung compared to the control lung. Such thickening was observed throughout the injured lung of this rat and is representative of what could be observed in the injured lungs of all the treated rats. Masson's stained slides showed similar thickening patterns and reflected increased collagen deposition, particularly at longer post-instillation times. The histological findings and RBC/barrier mismatch found in the images are summarized in Table 1.

TABLE 1

HISTOLOGY

| Animal/Status | | RBC/Barrier | Histology Findings | | | | |
|---|---|---|---|---|---|---|---|
| ID | Injury/days | Mismatch | Left | Cranial | Middle | Caudal | Accessory |
| 1 | control | None | NA | NA | NA | NA | NA |
| 2 | LL 15 Sham | None | NA | NA | NA | NA | NA |
| 3 | LL 15 | LL apex, base | 30% | NA | NA | NA | NA |
| 4 | LL 13 | LL apex, base, medial | 60% | 0% | 0% | 0% | 0% |
| 5 | LL11 | LL apex, base | 50% | 0% | 0% | 0% | 0% |
| 6 | LL 8 | LL apex, base | 40% | NA | NA | NA | NA |
| 7 | RL 15 | RL base | 0% | 25% | 30% | 50% | 40% |
| 8 | RL 7 | RL apex, base | 0% | 40% | 40% | 60% | NA |
| 9 | RL 5 | RL base, LL medial | 5% | 5% | 40% | 75% | 40% |

Regions of RBC/barrier mismatch were always associated with findings of injury on histology. In one right-lung instilled animal (#9), a small region of RBC/barrier mismatch (2×2 pixels) was noted in the medial apical region of the left lung. Histological examination of the left lung confirmed the presence of a small region of injury, which had presumably resulted from an incidental drop of bleomycin contamination during right lung instillation. This finding provides an early indicator of the sensitivity of the technique.

Table 1 is a summary of RBC/barrier mismatch seen with $^{129}$Xe imaging compared to histological findings in each lung lobe. The left lung consists of one lobe, whereas the right lung contains the cranial, middle, caudal, and accessory lobes. Note that in each image with RBC/barrier signal mismatch, corresponding injury was found in that region of the lung on histology. Histological sections for each lobe were evaluated by visual inspection to provide a semi-quantitative measure of the injured fraction. Some regions of injury found on histology were not immediately apparent from RBC/barrier mismatch. Those regions of injury could have been so consolidated that they were no longer ventilated and thus exhibit no signal in any of the compartments.

Figure 4:
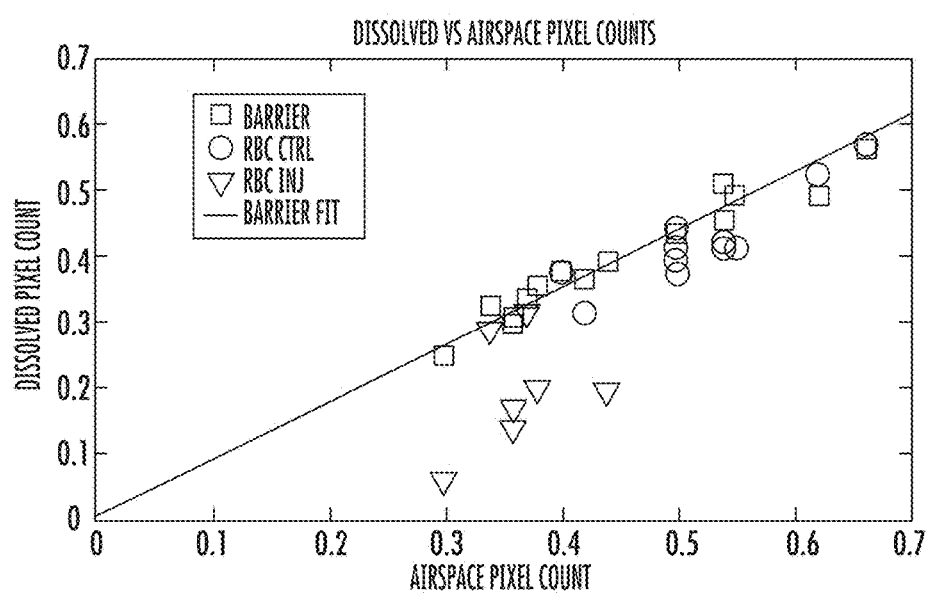
FIG. 4 is a graph of a ratio of normalized $^{129}$Xe pixel count in barrier and RBC images versus pixel count in the airspace images of each lung. The graph also includes a regression line that is fit to all of the barrier pixel counts in injured and uninjured lungs.

The close matching of barrier images with the airspace images is illustrated in FIG. 4 where the pixel counts from the barrier and RBC images are plotted against the airspace pixel counts for the right and left lungs of all animals. Barrier pixel counts closely matched the airspace pixel counts in both control and injured lungs with $R^2=0.93$, and a slope of 0.88±0.02 represented by the regression line. The slope of less than unity results from smaller average lung inflation during dissolved phase imaging, which was performed over the entire breathing cycle, versus airspace imaging which was performed at full inspiration. The observed matching is consistent with the fact that the barrier compartment is adjacent to the airspace compartment.

FIG. 4 is the ratio of normalized $^{129}$Xe pixel count in barrier and RBC images versus pixel count in the airspace images in each lung. Pixel counts were separated by right and left lung to take into account reduced lung volume in injured lungs and to allow one lung to serve as a control. As noted above, a strong correlation ($R^2=0.93$) is seen between barrier and airspace pixel counts (as would be expected since these compartments are adjacent to one another). The regression line is a fit to all the barrier pixel counts in injured and uninjured lungs. Also shown are the RBC pixel counts for control and injured lungs. In control lungs, the RBC pixel count correlated well with airspace counts ($R^2=0.83$), and as expected, in injured lungs it correlated poorly ($R^2=0.14$). Note that 5 of the 7 injured lung RBC pixel counts fall far below the regression line and thus represent severe mismatch. In two of the animals with right lung injury (#7 and #9) no measurable mismatch was observed. In these animals it appears that the bleomycin instillation created a complete ventilation block in the region of injury and thus likely obscured any RBC/barrier mismatch by preventing $^{129}$Xe from reaching the area.

Figures 5A, 5B:
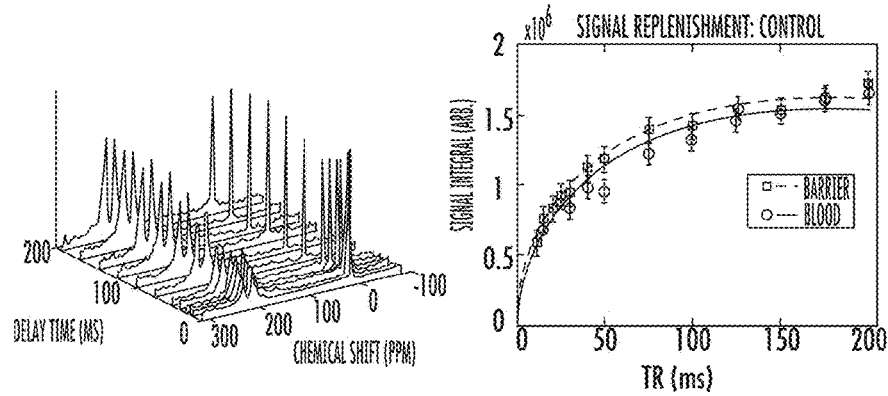
Figures 5C, 5D:
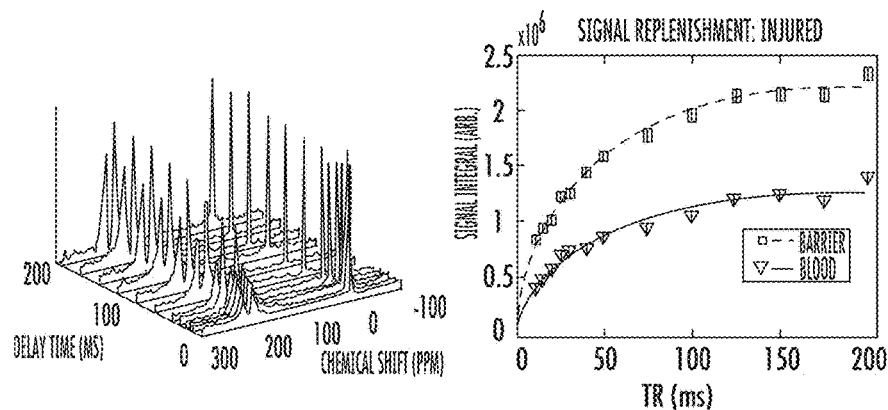

FIG. 5 shows the dynamic spectroscopy of $^{129}$Xe replenishment into the barrier and RBC compartments (dynamic spectra and corresponding fit) covering the entire lung of both a healthy control (#1) animal (FIGS. 5A, 5B) and right-lung-injured (#9) rat (FIGS. 5C, 5D), 5 days post-instillation. Note that the ratio of RBC/barrier signal at saturation is markedly diminished in the injured animal (FIG. 5D) versus the control animal (FIG. 5B).

While the shapes of the replenishment curves (and thus values of L and $L_c$ derived from curve fitting) were indistinguishable between the healthy and treated rat, the ratio of saturation RBC signal to barrier signal was dramatically different. The control animal showed an RBC/barrier=0.92 versus the injured animal with RBC/barrier=0.57. Thus, the RBC/barrier ratio derived from spectroscopy may be sensitive to alveolar-capillary gas transfer, though it lacks the spatial specificity of imaging. For completeness, the values of L and $L_c$ derived from curve fitting of data from all rats were L=5.5±0.4, $L_c$=5.1±0.6 assuming D=0.33×10$^{-5}$ cm$^2$s$^{-1}$, which are plausible values for healthy lung.

A notable feature of the XACT imaging technique is that regions showing barrier intensity, but no RBC intensity (RBC/barrier mismatch), corresponded to regions of barrier thickening found on histology. Thus, RBC/barrier ratios represent a simple and useful means of quantifying and comparing degrees of injury from the images. Table 2 summarizes the RBC/barrier ratios derived from imaging and spectroscopy in all the animals studied. The image-derived RBC/barrier ratio from the injured lungs was 0.59±0.24, which was significantly reduced (p=0.002) from the RBC/barrier ratio of 0.95±0.10 in the control lungs. The spectroscopy-derived RBC/barrier ratio was 0.69±0.12, which was also significantly reduced (p=0.02) compared to the RBC/barrier ratio determined from 5 healthy control rats (not shown in table) with a ratio of 0.87±0.14. It is postulated that there should be correspondence between the RBC/barrier ratios derived from the images and spectra in a given animal, sin ce spectra simply represent a collapse of the phase-sensitive image into its spectral components. This correspondence appears to exist in most of the rats studied. However, for the two rats with right lung injury and ventilation blockage (#7 and #9), the whole lung image-derived RBC/barrier ratio appeared normal whereas the spectroscopy-derived ratio was markedly reduced. The discrepancy in these two animals between imaging and spectroscopy is not fully understood, but could be a result of spectroscopy being performed at full inspiration where capillary blood volume could be reduced in injured areas.

TABLE 2

RATIOS

| Animal/Status | | RBC/Barrier Ratios | | | |
|---|---|---|---|---|---|
| ID | Injury/Days | Inj Lung | Ctrl Lung | Whole | Spectra |
| 1 | control | NA | 0.95 | 0.96 | 0.92 |
| 2 | LL 15 Sham | 0.88 | 0.94 | 0.92 | 0.84 |
| 3 | LL 15 | 0.51 | 0.88 | 0.70 | 0.81 |
| 4 | LL 13 | 0.55 | 1.02 | 0.85 | 0.78 |
| 5 | LL11 | 0.45 | 1.06 | 0.83 | 0.83 |
| 6 | LL 8 | 0.25 | 0.85 | 0.65 | 0.67 |
| 7 | RL 15 | 0.89 | 1.01 | 0.95 | 0.69 |
| 8 | RL 7 | 0.56 | 0.80 | 0.71 | 0.51 |
| 9 | RL 5 | 0.93 | 1.03 | 0.99 | 0.57 |

Table 2 provides a summary of RBC/barrier ratios derived from imaging and spectroscopy. The image-derived RBC/barrier ratio is significantly reduced (p=0.002) in all injured lungs relative to control lungs. Similarly, the mean spectroscopy-derived RBC/barrier ratio of 0.69±0.12 in treated animals is significantly reduced (p=0.02) compared to a value of 0.87±0.14 found in 5 healthy controls (not shown in table). The RBC/barrier ratios calculated from the images of both lungs compare relatively well with those determined by spectroscopy with the exception of two animals. In those two right lung injured animals (#7 and #9), bleomycin injury appeared to block ventilation, thus preventing regions of RBC/barrier mismatch from contributing to the images.

The barrier/RBC images result from dissolved-phase $^{129}$Xe and not mere airspace $^{129}$Xe signal contamination. First, it is noted that a barrier/RBC image SNR (6.8±2) and resolution (1.25×1.25 mm$^2$) versus air space image SNR (9.1±2) and resolution (0.31×0.31 mm$^2$) are consistent with known solubility and tissue density differences. From the airspace images, dissolved images lose a factor of 100 in each of the barrier/RBC compartments and a factor of √2 due to higher bandwidth. Signal gains of a factor 3 due to increased flip angle, and $\sqrt{2400/400}$ from signal averaging leave a barrier and RBC signal strength of about 1/20 of the airspace, which when spread out spatially suggests a possible image resolution of 1.3×1.3 mm$^2$—which is what has been achieved. Second, the absence of the major airways in the barrier/RBC images is noted, which is consistent with the expectation that gas exchange is most prominent in the alveoli (18). Third, the gas phase signal is nearly 5 kHz away from the barrier/RBC resonances, where the scanner is tuned. In radial imaging, such off-resonant artifacts manifest themselves as a halo around the primary image (25), and no such halo is observed.

The 211 ppm and 197 ppm compartments have been substantially completely separated by the imaging methods described. Evidence of this separation is the clearly reduced $^{129}$Xe RBC signal in the injured lungs, an observation that is entirely consistent with predictions based on the disease model. Meanwhile, the barrier compartment images always matched closely to the airspace images as expected given their adjacent location. Further evidence that the RBC/barrier compartments are separated stems from the reasonably good correlation (R$^2$=0.83) between RBC/barrier ratios derived from imaging versus the same ratio derived from spectroscopy in 7 of the 9 images (excluding two animals with blocked ventilation). One cannot rule out some residual overlap of the RBC/barrier resonances in the images. For example, significant RBC image intensity is not observed in the right accessory lobe of the uninjured lungs. This lobe, which curls around the heart, likely experiences a slightly reduced B$_0$ field due to the large blood volume of the heart, thus retarding the RBC signal phase in this lobe back to the barrier channel. A possible correction for these undesired phase shifts is to use phase-sensitive images of $^{129}$Xe in the airspace to create a field map to correct these distortions as will be discussed further below. Since airspace images are derived from just the 0 ppm resonance, any phase shifts are only attributable to B$_0$ variations.

It is not believed that the reduced RBC signals are the result of shortened $^{129}$Xe relaxation times T$_1$, T$_2$ or T$_2$* post injury rather than the proposed diffusion barrier thickening. To cause the reduced intensity in the RBC images, a T$_1$ relaxation time on the order 50 ms is used. While in vivo $^{129}$Xe relaxation times less than 4 s have not been reported in the literature, such rapid relaxation could be caused either by a dramatically increased concentration of paramagnetic centers or lengthened correlation times resulting from reduced $^{129}$Xe mobility in regions of injury. If by some means an excess of free radicals occurred in regions of injury, this would likely affect both the RBC and barrier compartments equally. Conceivably, $^{129}$Xe binding to collagen deposits associated with fibrosis could result in reduced $^{129}$Xe mobility accompanied by a reduction in both T$_1$ and T$_2$, which could result in signal attenuation. However, such relaxation would affect the barrier compartment, not the RBC compartment, opposite from the effect required to explain our observations.

It is not believed that the RBC/barrier mismatch effect could be partially caused by reduced capillary density or blood volume rather than increased diffusion barrier thickness. However, such a possibility is not definitively excluded as a contribution from capillary destruction based on the data. Stained sections do show areas of lung that are so severely injured as to be fully consolidated, lack alveoli, airways, and capillaries and, thus, would not contribute $^{129}$Xe signal in any of the compartments. Other areas of injured lung clearly have intact alveoli with thickened alveolar septa and also have capillaries and RBCs. Although it is possible that a reduction of blood volume in the injured lung may contribute to the absent RBC signal, the overriding factor appears to be the diffusional delay due to interstitial thickening.

Dynamic spectroscopy also appears to be sensitive to gas exchange efficiency, although the effect does not appear as yet to be as powerful as imaging. However, the limited gas usage and simplicity of spectroscopy merit its continued consideration. A useful extension of spectroscopy may be to acquire airspace $^{129}$Xe signals with well defined flip angle which could then be used to quantify the increased 197 ppm and decreased 211 ppm signal intensities relative to controls.

Whole lung spectroscopy may not directly validate the model of RBC signal delay, sin ce any regional delay is averaged out by healthy lung regions. However, with increased hyperpolarized $^{129}$Xe production, dissolved $^{129}$Xe images could be generated at multiple TR values, effectively creating localized dynamic spectroscopic information which would allow regional curve fitting of the 197 and 211 ppm pixel intensities to equations 4 and 5 to extract meaningful values for L, $L_c$ and D on a pixel-by-pixel basis.

As shown in FIG. 1D, a thickening of the barrier by 6.5 μm can create about a 600% attenuation in the RBC replenishment (at 50 ms TR), while only reducing a 75 μm diameter rat alveolus to roughly 62 μm and likely reducing ADC (35, 36) by less than 20%. Similarly, the ability to distinguish barrier and RBC could make XACT more sensitive that prior art techniques to interstitial thickening. Since the XTC (13, 18) contrast comes from the total increase in tissue volume, the same example of 6.5 μm thickening would cause a roughly 60% increase in the XTC effect.

XACT is likely to be more sensitive to either ADC imaging or XTC imaging to changes in barrier thickness. In the past, pulmonary fibrosis in the clinical setting is often detected and monitored using high-resolution CT (38), although significant challenges remain (39) and more invasive surgical lung biopsy remains the gold standard (40). Embodiments of the present invention provide methods that are sensitive to micron-scale changes in the blood/gas barrier thickness and thus may provide increased sensitivity and specificity compared to CT, particularly in early disease. Furthermore, the substantially non-invasive nature of the method should allow for monitoring of patients and their response to therapeutic intervention.

Embodiments of the invention can be used to generate 3D clinical images. To obtain the 3-D images larger volumes of $^{129}$Xe gas relative to those used in the rat evaluations and/or higher polarization levels can be used. Also, a lower diffusion coefficient for the barrier/RBC resonances may allow more efficient multi-echo sequences to be used in order to extract more signal from the limited dissolved $^{129}$Xe magnetization, although $^{129}$Xe exchange may hamper this prospect. Third, further discrimination of the barrier/RBC resonances can be achieved by correcting these images using a field map generated from the single-resonance airspace $^{129}$Xe image. This technical development can facilitate clinical application to subjects where the increased imaging volume may lead to larger phase distortions.

Although in small animals, images are routinely acquired over multiple breaths, a human subject can inhale ~1 liter of $^{129}$Xe in a single breath, enabling equivalent anatomical resolution images to be generated. To image gas-exchange in 3D, projection-reconstruction imaging (projection encoding in 3D) can be used. Projection-reconstruction imaging in 2D of dissolved $^{129}$Xe replenishment has required relatively small volumes of hyperpolarized $^{129}$Xe (~150 ml). To overcome the very short transverse relaxation time $T_2$* of dissolved $^{129}$Xe (~1.7 ms), projection reconstruction (PR) imaging can be used (41). PR is well suited to short T2* environments due to its ultra-short echo times. Furthermore, the single-point Dixon technique used to create separate images of 129Xe in the barrier vs. the RBCs can operate with an echo time of only ~800 μs. Thus, for 3D imaging, PR sampling of Fourier space can be used.

Like 2DPR, 3DPR is capable of 800 μs echo times to create 90° separation between the 197 ppm and 211 ppm resonances. 3D projection encoding uses more radial projections than 2D projection encoding, and thus may need additional $^{129}$Xe gas. To facilitate 3D sampling for $^{129}$Xe gas exchange, imaging 3D projection encoding with phase-sensitive reconstruction can be used and also, an efficient 3D k-space trajectory model can be used, reducing the number of radial views.

An example of a conventional 3D projection trajectory is shown in FIG. 10A. FIG. 10B illustrates a more efficient 3D trajectory. This trajectory was developed by Song, et al. (42) and requires 9329 frames to produce a 64×64×16 image matrix, a 30% reduction in the number of frames required by the conventional 3DPR code. The frames can be supplied by about 750 ml of hyperpolarized $^{129}$Xe or about 466 breaths. This efficient reconstruction approach can eliminate the typical re-gridding of the k-space data to a Cartesian space. Instead, a direct, nonuniform Fourier transform is used which removes constraints on the k-space trajectory and makes the efficiency possible.

Improved RBC/Barrier separation can be obtained. $^{129}$Xe signal in the 197 ppm barrier compartment and the 211 ppm RBC compartment are, to first order, well-separated on phase-sensitive imaging. As discussed above, a disease model has shown to increase the thickness of the blood/gas barrier and, as predicted, the RBC uptake image (211 ppm) showed regions of signal deficit, whereas the barrier uptake image (197 ppm) closely matched the air space image. Also, the whole-lung ratio of RBC/barrier uptake calculated from imaging correlated well ($R^2$=0.64) with the RBC/barrier uptake ratio from dynamic spectroscopy.

However, the RBC/barrier separation is not perfect. One notable example is the absence of the right accessory lobe from the RBC uptake images even in control rats. This lobe, which curls around the front of the heart, experiences a slightly reduced $B_0$ due to the high susceptibility of blood in the heart compared to lung tissue. While planned extensions to 3D imaging will eliminate some of the distortions, methods can be used to correct for them. This correction may be useful for extension to clinical imaging.

As discussed above, to separate RBC/barrier uptake imaging, a 1-point Dixon technique has been used. This simple implementation of the Dixon technique assumes that the frequency variation during the "echo time" is only dependent on the chemical shift difference between the two species. This over-simplification assumes essentially perfect $B_0$ homogeneity over the entire sample. Particularly in the lung, such perfection is typically unattainable. For fat/water separation, numerous variants of the Dixon technique (2-point Dixon [43], 3-point Dixon [41]) have emerged to try to de-convolute the desired chemical shifts from unintended phase shifts arising from $B_0$ field distortions.

Unfortunately, these more sophisticated versions of the Dixon technique are not suitable for application in the short $T_2$* environment of the lung because all require images made at several increasingly long echo times. In the lung, where $T_2$* is only 1.7 ms at a 2 T field, the attenuation at the second echo time is too great. Thus, a 1-point Dixon technique with ultra-short echo time is better suited for the application. Fortunately, $B_0$ inhomogeneity corrections can be made by using the ability to make an entirely separate image of $^{129}$Xe in the air-space. Since the airspace image comes from only one $^{129}$Xe resonance, phase differences can be attributed to $B_0$ fluctuations.

In some embodiments, to correct the RBC/barrier images, an electronic map or maps of air space phase variation can be generated using phase-sensitive $^{129}$Xe ventilation images. The phase map can be constructed from the ratio of imaginary to real image channels according to $\tan(\phi(x,y))=IM(x,y)/RE(x,y)$. A preliminary version of such a map, generated from a non-slice selective image, is displayed in FIG. 11C. Note the accessory lobe has a −40° phase shift, while the trachea has +50° phase shift. The phase map may be in color as indicated by the graduated color chart (shown in black and white) indicating phase variation. A visual map need not be created; only the spatial and phase data can be directly applied to correct the dissolved phase $^{129}$Xe image data. FIG. 11A illustrates a real channel image. FIG. 11B illustrates an imaginary channel image. FIG. 11C is the phase map generated from the airspace image. The phase variations in the image map are due to $B_0$ inhomogeneity and can be used to correct barrier/RBC $^{129}$Xe images.

$B_0$ maps with 3D projection encoding, or a series of 2D slices ($T_2^*$ is sufficiently long for gas phase $^{129}$Xe to use slice selective pulses), can be generated. Data used to generate the RBC/barrier images can be corrected using either the raw phase map, or if unduly noisy, phase variation can be fit to a smoothed function. The resolution of the phase maps must be only as high as the dissolved phase image resolution, anticipated at 1×1×5 mm$^3$ for rats and about 10×10×10 for humans. Thus, generating them need not consume undue amounts of the hyperpolarized $^{129}$Xe.

For dissolved phase imaging, the MRI receiver phase is set via whole-lung spectroscopy, such that the 211 ppm RBC resonance corresponds to the real channel, and the 197 ppm resonance lags 90° behind in the negative imaginary channel (FIG. 12A). Thus, a simple one-to-one correspondence of the real channel to the 211 ppm, and imaginary channel to 197 ppm resonance can be assumed along the lines of Equation (6):

$$\begin{pmatrix} S_{211} \\ S_{197} \end{pmatrix} = \begin{pmatrix} 1 & 0 \\ 0 & -1 \end{pmatrix} \begin{pmatrix} \text{Re} \\ \text{Im} \end{pmatrix} \quad [6]$$

In fact, when phase variations $\phi$ due to $B_0$ distortion are taken into account (FIG. 12B), the mapping function becomes as expressed in Equation (7):

$$\begin{pmatrix} S_{211} \\ S_{197} \end{pmatrix} = \begin{pmatrix} \cos\phi & \sin\phi \\ \sin\phi & -\cos\phi \end{pmatrix} \begin{pmatrix} \text{Re} \\ \text{Im} \end{pmatrix} \quad [7]$$

In initial $^{129}$Xe uptake imaging studies, −40° phase shifts have caused the right accessory lobe to disappear from the RBC image. Because the 197 ppm resonance is captured in the negative imaginary channel, its −40° shift subtracts from the real channel. The correction scheme described should eliminate such undesired mixing and will be most effective if the phase shifts fall between −180° and 180°, although unwrapping of larger phase-shifts is possible [63]. The non-slice-selective images exhibit only ±40° phase shifts and further reductions can be expected when thinner slices are used. The relatively small phase shifts, even in the hostile lung environment, are a paradoxical benefit of the small $^{129}$Xe gyromagnetic ratio.

FIGS. 13A and 13B are sets of images taken of a healthy rat at various TR values. FIG. 13A are barrier images taken (from left to right) at TR=10, 15, 25, 50 ms. The images in FIG. 13B are of the RBC and were taken at the same TR intervals. By acquiring dissolved $^{129}$Xe images at multiple repetition times, typically at least three, and more typically between 3-5 different TR times, with TR values between about 10 ms to about 60 ms (for example, 10, 20, 30, 40, 50 ms), sufficient data can be obtained to curve-fit the signal replenishment on a pixel-by-pixel basis to extract quantitative measures of barrier thickness and/or $^{129}$Xe diffusion coefficient.

Figure 6:
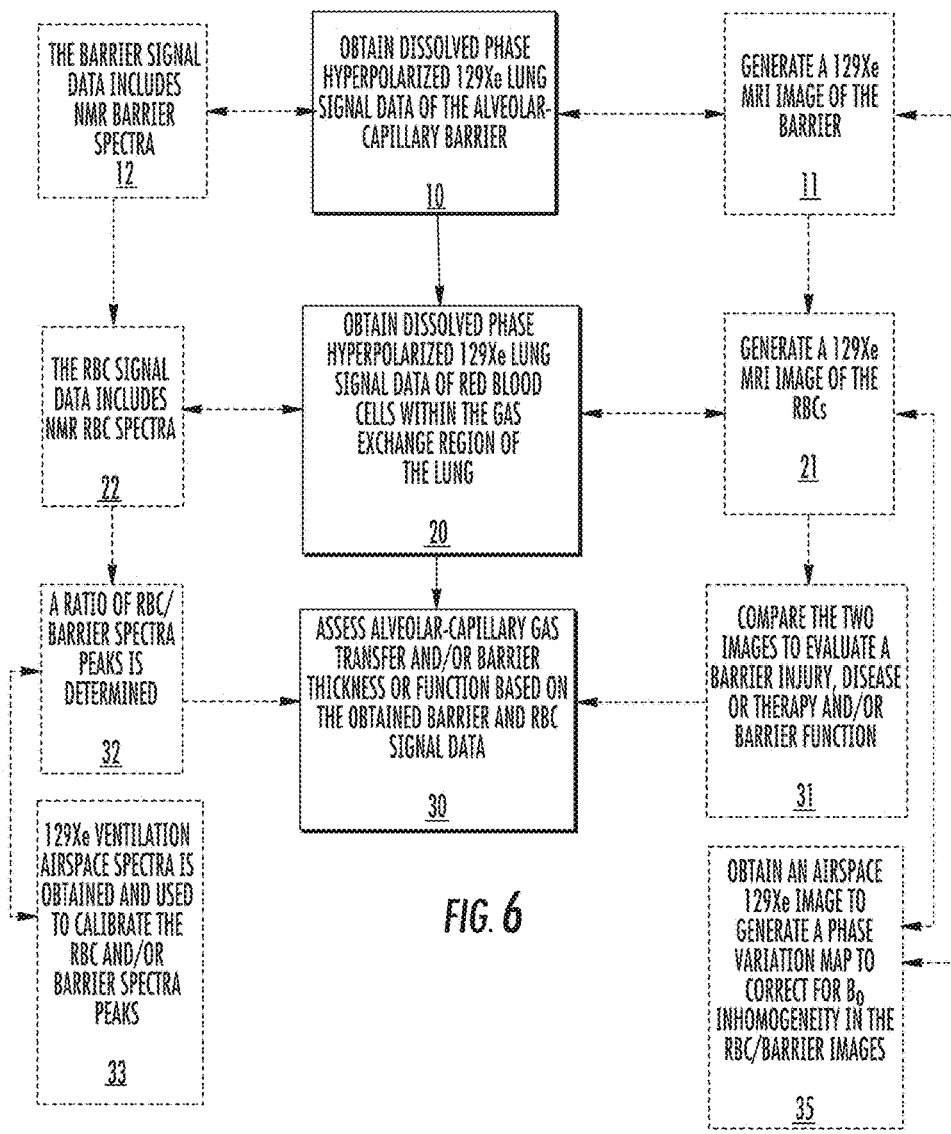
FIG. 6 is a flow chart of exemplary operations that can be used to carry out methods according to some embodiments of the present invention.

FIG. 6 is a flow chart of exemplary operations that may be used to carry out embodiments of the present invention. As shown, dissolved phase $^{129}$Xe signal data of the alveolar capillary barrier are obtained (block 10). Similarly, dissolved phase $^{129}$Xe signal data of red blood cells within the gas exchange regions of the lung (proximate the barrier) are obtained (block 20). Alveolar-capillary gas transfer can be assessed based on the obtained barrier and RBC signal data (block 30).

The respective data can be used to generate an MRI image of the barrier (block 11) and MRI image of the RBCs (block 21). The two images can be compared to evaluate a barrier injury, disease or therapy (i.e., thickness or thinning) and/or function. A $^{129}$Xe airspace image can be obtained to generate a phase variation map and data from the phase variation map can be used to correct $B_0$ inhomogeneity induced phase variations in the RBC and barrier images (block 35).

Once the $^{129}$Xe gas is dissolved, it no longer has such a massive diffusion coefficient. So one may elect to employ pulse sequences like spin-echo imaging instead of radial imaging. A 64×64 spin echo image can be acquired using only 64 rf excitations (vs 200 with radial imaging). Also, multiple spin echoes can be employed to improve SNR.

Alternatively, or additionally, the data can comprise NMR barrier spectra (block 12) and RBC spectra (block 22). A ratio of the RBC peak size to barrier peak size can be determined and used to assess gas transfer and/or lung health (block 32). An airspace $^{129}$Xe NMR spectra can also be obtained and used to calibrate the RBC and/or barrier peaks (block 33).

Figure 7:
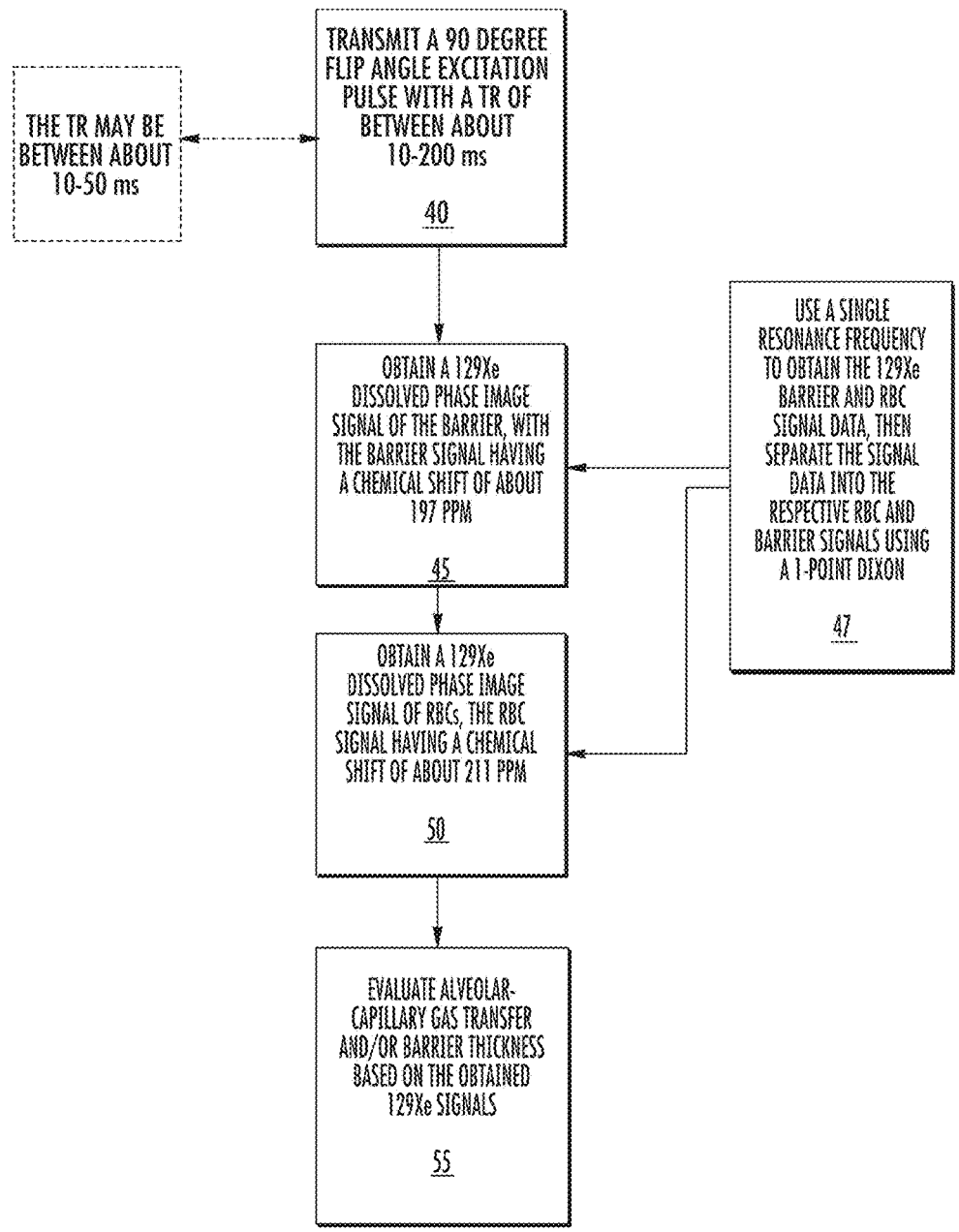
FIG. 7 is a flow chart of steps that can be used to carry out embodiments of the present invention.

FIG. 7 is a flow chart of steps that can be used to carry out certain embodiments of the invention. As shown, a 90 degree flip angle excitation pulse is transmitted with a pulse repetition time TR between about 40-60 ms. $^{129}$Xe dissolved phase images of the barrier and of the RBC are obtained, (block 45) and (block 50), respectively, based on the excitation of the pulse. The two images can be generated using the same excitation (resonance) frequency by separating image signal data using a 1-point Dixon technique (block 47). Alveolar-capillary transfer and/or barrier status based on the obtained images (block 55).

It is noted that although a 1-point Dixon technique has been used to decompile or separate the image signal data as discussed herein, other Dixon or signal processing techniques, modified to work with the short hyperpolarized xenon relaxation times (the signal can decay in a few milliseconds) in the lung may be used, such as, for example a modified 2-point Dixon.

Figure 8:
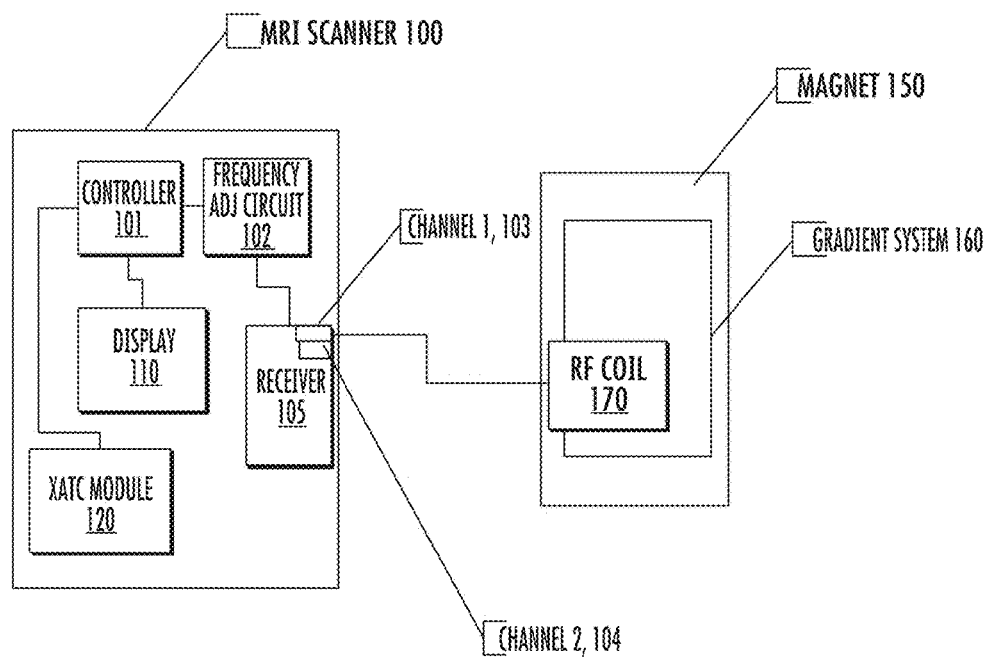
FIG. 8 is a schematic illustration of an MRI scanner according to embodiments of the present invention.

FIG. 8 is a schematic diagram of an MRI scanner 100 with a superconducting magnet 150, a gradient system 160 and an RF coil 170 that communicates with an RF amplifier (not shown) associated with the MRI scanner as is well known to those of skill in the art. As also shown, the MRI scanner includes a multi-channel receiver 105 with channel 1 103, which can be the real channel, and channel 2 104, which can be the imaginary channel. Signal from the RF coil 170 may be transmitted to the receiver 105 via a cable (typically a BNC cable) where the signal can be decomposed into the two channels 103, 104. The MRI scanner 100 also includes a controller 101, a frequency adjustor circuit 102 that can tune the MRI scanner to generate a desired RF excitation frequency, and a display 110. The display 110 may be local or remote. The display 110 can be configured to display the RBC and barrier images substantially concurrently, or as an image that considers image data from both (and magnetic field inhomogeneity correction as appropriate), to provide a 3-D image of the gas-exchange regions of the lung.

The MRI scanner 100 can also include an XATC operational module 120, which can programmatically communicate with the frequency adjustor circuit 102 and receiver 105 to electronically (automatically) switch operational modes, frequencies, phases and/or electronically direct the excitation and acquisition of appropriate signals, and generate the XATC images and/or NMR spectra evaluation according to some embodiments of the invention. See description above for the frequency of gas (MHz) with the dissolved phase $^{129}$Xe shifted higher in Hz according to the magnetic field strength of the system.

In some embodiments, the module 120 can be configured to form a curve fit to extract phases and frequencies of the 197 ppm and 211 ppm peaks then automatically set channel 1 (the real channel) so that the RBC image comes from channel 1 103 and the barrier image comes from channel 2 104 (the imaginary channel), although the reverse may also be used. The automated software routine can take a few spectra, then automatically set the scanner frequency and phase to XACT imaging and apply the desired excitation pulse and TR times. The module 120 may also be configured to generate the images using radial imaging and/or spin echo imaging noted above. The module 120 can be configured to generate a phase variation map using image data of a $^{129}$Xe ventilation image of the lung and programmatically electronically correct phase errors in RBC and barrier image data.

In some embodiments, the MRI scanner 100 can be configured to obtain image signal data in an interleaved manner to generate dissolved and airspace images. In some embodiments, two batches or breath-hold deliveries of $^{129}$Xe can be used. That is, one batch of gas may make the airspace image, and one batch of gas may make the dissolved image. However, in some embodiments, a scanning sequence can be used that switches the scanner frequency from gas to dissolved phase and back again and acquires portions of the gas and dissolved image data sets in an interleaved manner.

Figure 9A:
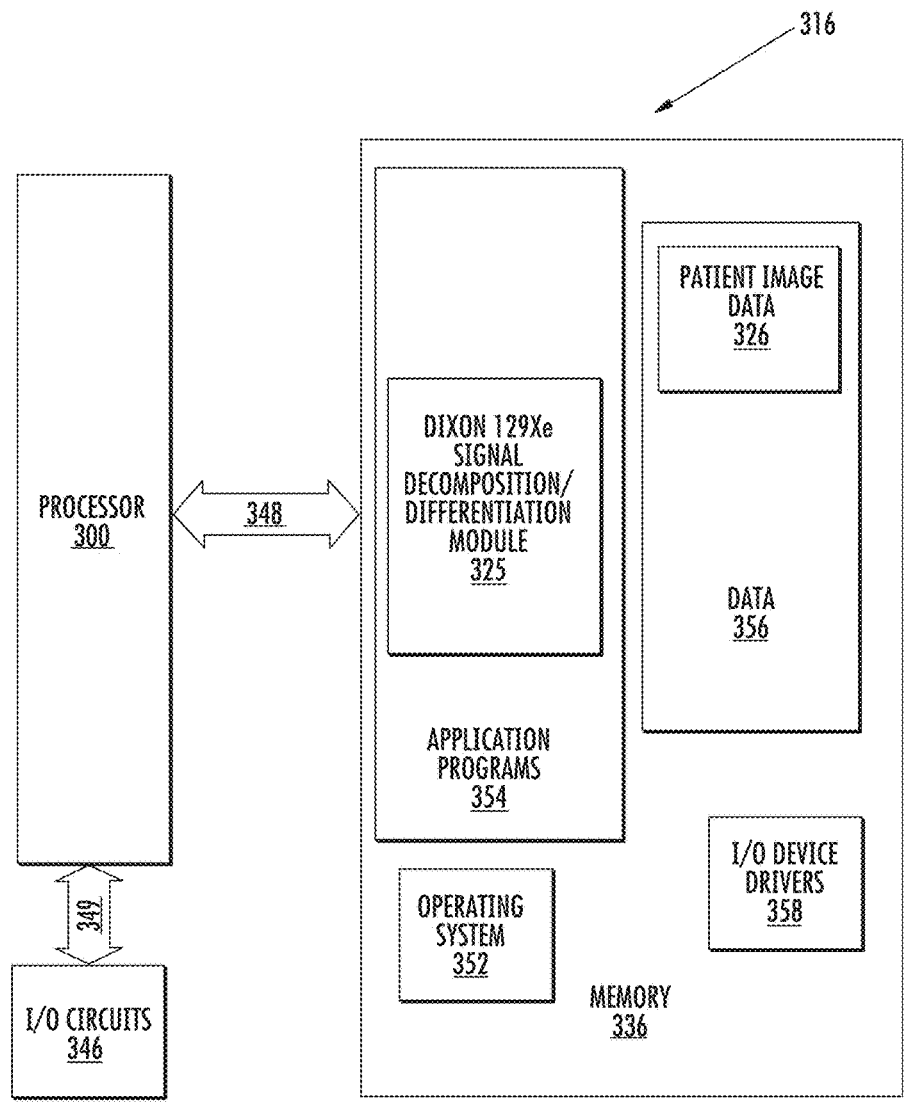
FIG. 9A is a block diagram of data processing systems that may be used to generate $^{129}$Xe images in accordance with some embodiments of the present invention.
Figure 9B:
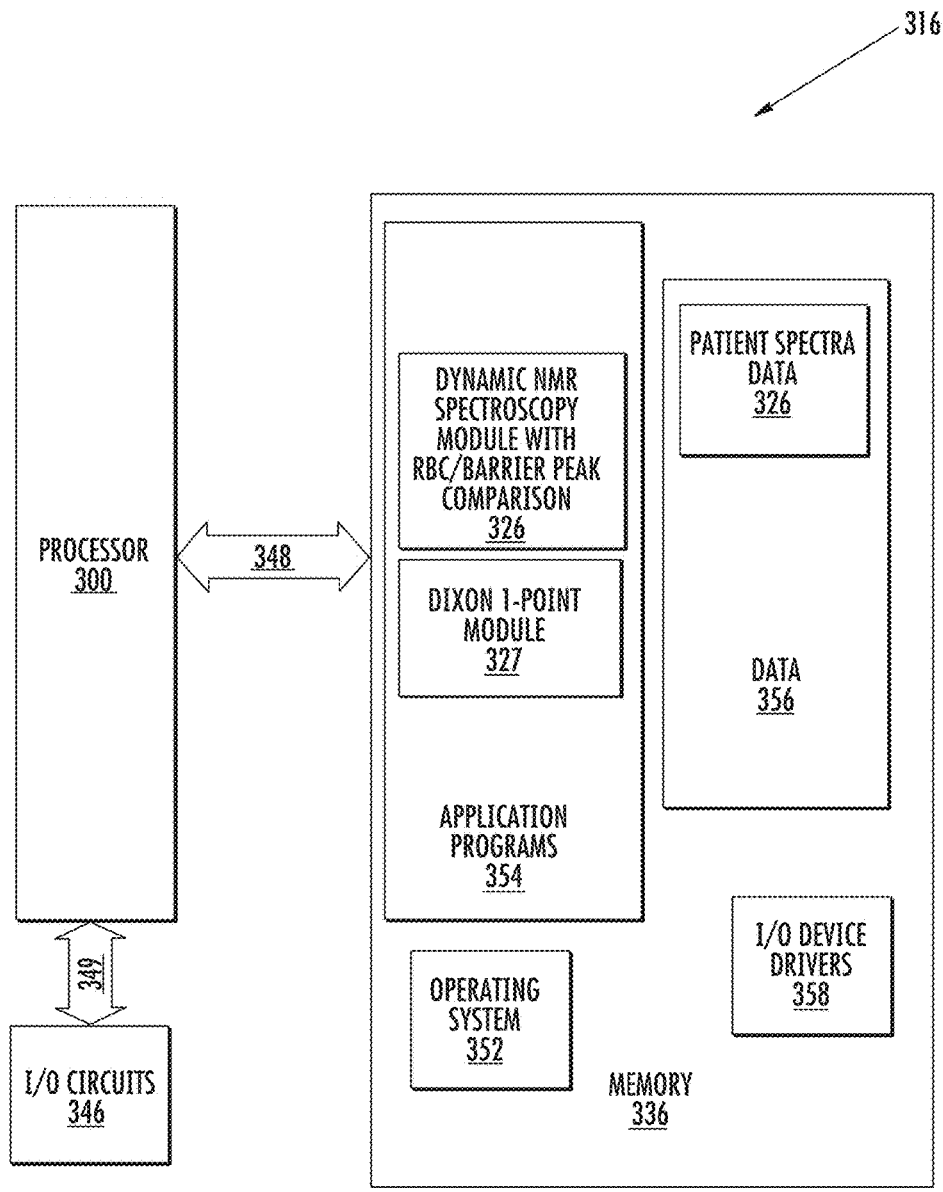
FIG. 9B is a block diagram of data processing systems that may be used to generate $^{129}$Xe gas transfer ratios of pixels associated with RBC and barrier spectra accordance with some embodiments of the present invention.

Referring now to FIGS. 9A and 9B, a data processing system 316 is shown that may be used to provide the $^{129}$Xe dissolved phase MRI signal decomposition (FIG. 9A) or the NMR spectra evaluation module (FIG. 9B). Thus, in accordance with some embodiments of the present invention, the system 316 comprises a memory 336 that communicate with a processor 300. The data processing system 316 may further include an input/output (I/O) circuits and/or data port(s) 346 that also communicate with the processor 300. The system 316 may include removable and/or fixed media, such as floppy disks, ZIP drives, hard disks, or the like, as well as virtual storage, such as a RAMDISK. The I/O data port(s) 346 may be used to transfer information between the data processing system 316 and another computer system or a network (e.g., the Internet). These components may be conventional components, such as those used in many conventional computing devices, and their functionality, with respect to conventional operations, is generally known to those skilled in the art.

FIGS. 9A and 9B illustrate the processor 300 and memory 336 that may be used in embodiments of systems in accordance with some embodiments of the present invention. The processor 300 communicates with the memory 336 via an address/data bus 348. The processor 300 may be, for example, a commercially available or custom microprocessor. The memory 336 is representative of the one or more memory devices containing the software and data used for providing $^{129}$Xe MRI image data or $^{129}$XE NMR spectra data in accordance with some embodiments of the present invention. The memory 336 may include, but is not limited to, the following types of devices: cache, ROM, PROM, EPROM, EEPROM, flash, SRAM, and DRAM.

As shown in FIGS. 9A and 9B, the memory 336 may contain up to two or more categories of software and/or data: an operating system 352, I/O Device Drivers 358, data 356 and application programs 354. FIG. 9A illustrates that the data 356 can include patient image data 326 and FIG. 9B illustrates that data 356 can include patient NMR spectra data 326'.

As will be appreciated by those of skill in the art, the operating system 352 may be any operating system suitable for use with a data processing system, such as IBM®, OS/2®, AIX® or zOS® operating systems or Microsoft® Windows®95, Windows98, Windows2000 or WindowsXP operating systems Unix or Linux™. IBM, OS/2, AIX and zOS are trademarks of International Business Machines Corporation in the United States, other countries, or both while Linux is a trademark of Linus Torvalds in the United States, other countries, or both. Microsoft and Windows are trademarks of Microsoft Corporation in the United States, other countries, or both. The input/output device drivers 358 typically include software routines accessed through the operating system 352 by the application programs 354 to communicate with devices such as the input/output circuits 346 and certain memory 336 components. The application programs 354 are illustrative of the programs that implement the various features of the circuits and modules according to some embodiments of the present invention. Finally, the data 356 represents the static and dynamic data used by the application programs 354 the operating system 352 the input/output device drivers 358 and other software programs that may reside in the memory 336.

As further illustrated in FIG. 9A, according to some embodiments of the present invention, application programs 354 may optionally include a Dixon Signal Decomposition and/or Signal Differentiation Module 325 that can be used to generate one or more of an RBC Image and/or a Barrier Image or differentiate the signal into the appropriate respective image data sets. FIG. 9B illustrates the application programs 354 which may optionally include a dynamic $^{129}$Xe dissolved phase spectroscopy module 327 that can obtain RBC spectra and barrier spectra and a peak comparison module 328. The application program 354 may be located in a local server (or processor) and/or database or a remote server (or processor) and/or database in the MRI scanner, or combinations of local and remote databases and/or servers.

While the present invention is illustrated with reference to the application programs 354 with Modules 325 (in FIG. 9A) and 327 and 328 (in FIG. 9B), as will be appreciated by those of skill in the art, other configurations fall within the scope of the present invention. For example, rather than being application programs 354 these circuits and modules may also be incorporated into the operating system 352 or other such logical division of the data processing system. Furthermore, while the application program 354 is illustrated in a single data processing system, as will be appreciated by those of skill in the art, such functionality may be distributed across one or more data processing systems in, for example, the type of client/server arrangement described above. Thus, the present invention should not be construed as limited to the configurations illustrated in FIG. 6 but may be provided by other arrangements and/or divisions of functions between data processing systems. For example, although FIGS. 9A and 9B are illustrated as having various circuits and modules, one or more of these circuits or modules may be combined or separated without departing from the scope of the present invention.

Although FIGS. 9A and 9B illustrate exemplary hardware/software architectures that may be used, it will be understood that the present invention is not limited to such a configuration but is intended to encompass any configuration capable of carrying out operations described herein. Moreover, the functionality of the data processing systems and the hardware/software architectures may be implemented as a single processor system, a multi-processor system, or even a network of stand-alone computer systems, in accordance with various embodiments of the present invention.

Computer program code for carrying out operations of data processing systems discussed above with respect to the figures may be written in a high-level programming language, such as Java, C, and/or C++, for development convenience. In addition, computer program code for carrying out operations of embodiments of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller.

The present invention is described herein with reference to flowchart and/or block diagram illustrations of methods, systems, and computer program products in accordance with exemplary embodiments of the invention. These flowchart and/or block diagrams further illustrate exemplary operations for administering and/or providing calendar-based time limited passcodes, in accordance with some embodiments of the present invention. It will be understood that each block of the flowchart and/or block diagram illustrations, and combinations of blocks in the flowchart and/or block diagram illustrations, may be implemented by computer program instructions and/or hardware operations. These computer program instructions may be provided to a processor of a general purpose computer, a special purpose computer, or other programmable data processing apparatus to produce a machine, such that the instructions, which execute via the processor of the computer or other programmable data processing apparatus, create means and/or circuits for implementing the functions specified in the flowchart and/or block diagram block or blocks.

These computer program instructions may also be stored in a computer usable or computer-readable memory that may direct a computer or other programmable data processing apparatus to function in a particular manner, such that the instructions stored in the computer usable or computer-readable memory produce an article of manufacture including instructions that implement the function specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the functions specified in the flowchart and/or block diagram block or blocks.

The flowcharts and block diagrams illustrate the architecture, functionality, and operations of some embodiments of methods, systems, and computer program products. In this regard, each block represents a module, segment, or portion of code, which comprises one or more executable instructions for implementing the specified logical function(s). It should also be noted that in other implementations, the function(s) noted in the blocks might occur out of the order noted. For example, two blocks shown in succession may, in fact, be executed substantially concurrently or the blocks may sometimes be executed in the reverse order, depending on the functionality involved.

In summary, embodiments of the invention can be used to create images of $^{129}$Xe dissolved in lung tissue barrier and red blood cells within the gas exchange regions of the lung. Embodiments of the invention can employ radial encoding, continuous $^{129}$Xe replenishment from the air spaces, and signal averaging, to overcome the short $T_2^*$ and low instantaneous $^{129}$Xe magnetization in the barrier and RBC phases. These images exhibit SNR and resolution that is consistent with expectations based on gas phase magnetization, xenon solubility, and tissue density. By separating the $^{129}$Xe image into barrier and RBC components, imaging of the alveolar-capillary gas transfer process a fundamental role of the lung, can be achieved. The images showing an absence of $^{129}$Xe replenishment in red blood cells in regions of injury are consistent with theoretical expectations based on decreased diffusion transfer of $^{129}$Xe from alveoli to red blood cells. Methods of quantifying gas transfer efficiency is also proposed by using the ratio of RBC/barrier pixel counts.

Some embodiments of the present invention have been illustrated herein by way of example. Many variations and modifications can be made to the embodiments without substantially departing from the principles of the present invention. All such variations and modifications are intended to be included herein within the scope of the present invention, as set forth in the following claims.

REFERENCES

1. Salerno, M., Altes, T. A., Mugler, J. P., Nakatsu, M., Hatabu, H. & DeLange, E. E. (2001) *Eur. J. Radiology* 40, 33-44.
2. Moller, H. E., Chen, X. J., Saam, B., Hagspiel, K. D., Johnson, G. A., Altes, T. A., de Lange, E. E. & Kauczor, H. U. (2002) *Magnetic Resonance In Medicine* 47, 1029-1051.
3. Garg, K., Welsh, C. H., Feyerabend, A. J., Subber, S. W., Russ, P. D., Johnston, R. J., Durham, J. D. & Lynch, D. A. (1998) *Radiology* 208, 201-208.
4. Hatabu, H., Gaa, J., Kim, D., Li, W., Prasad, P. V. & Edelman, R. R. (1996) *Magnetic Resonance In Medicine* 36, 503-508.
5. West, J. B. (1995) *Pulmonary Pathophysiology—The Essentials* (Williams & Wilkins, Baltimore).
6. Agusti, A. G. N., Roca, J., Gea, J., Wagner, P. D., Xaubet, A. & Rodriguezroisin, R. (1991) *American Review Of Respiratory Disease* 143, 219-225.
7. Weibel, E. R. (1984) *The Pathway for Oxygen—Structure and Function in the Mammalian Respiratory System* (Harvard University Press, Cambridge, Mass.).
8. Mansson, S., Wolber, J., Driehuys, B., Wollmer, P. & Golman, K. (2003) *Magnetic Resonance In Medicine* 50, 1170-1179.

9. Sakai, K., Bilek, A. M., Oteiza, E., Walsworth, R. L., Balamore, D., Jolesz, F. A. & Albert, M. S. (1996) *Journal Of Magnetic Resonance Series B* 111, 300-304.
10. Albert, M. S., Balamore, D., Kacher, D. F., Venkatesh, A. K. & Jolesz, F. A. (2000) *NMR in Biomedicine* 13, 407-414.
11. Ruppert, K., Brookeman, J. R., Hagspiel, K. D., Driehuys, B. & Mugler, J. P. (2000) *NMR in Biomedicine* 13, 220-228.
12. Abdeen, N., Cross, A., Cron, G., White, S., Rand, T., Miller, D. & Santyr, G. E. (2006) *Magnetic Resonance in Medicine* 56, 255-264.
13. Ruppert, K., Mata, J. F., Brookeman, J. R., Hagspiel, K. D. & Mugler, J. P. (2004) *Magnetic Resonance In Medicine* 51, 676-687.
14. Parent, R. A. (1992) in *Treatise on Pulmonary Toxicology*, ed. Parent, R. A. (CRC Press, Vol. 1.
15. Kitani, K. (1972) *Scand. J. Clin. Lab. Invest.* 29, 167-172.
16. Weathersby, P. K. & Homer, L. D. (1980) *Undersea Biomedical Research* 7, 277-296.
17. Swanson, S. D., Rosen, M. S., Coulter, K. P., Welsh, R. C. & Chupp, T. E. (1999) *Magnetic Resonance in Medicine* 42, 1137-1145.
18. Ruppert, K., Brookeman, J. R., Hagspiel, K. D. & Mugler, J. P. (2000) *Magnetic Resonance in Medicine* 44, 349-357.
19. Crank, J. (1975) *The Mathematics of Diffusion* (Oxford University Press, Oxford).
20. Wolber, J., Cherubini, A., Dzik-Jurasz, A. S. K., Leach, M. O. & Bifone, A. (1999) *Proceedings of the National Academy of Sciences of the United States of America* 96, 3664-3669.
21. Dimitrov, I. E., Reddy, R. & Leigh, J. S. (2000) *Journal of Magnetic Resonance* 145, 302-306.
22. Bifone, A., Song, Y. Q., Seydoux, R., Taylor, R. E., Goodson, B. M., Pietrass, T., Budinger, T. F., Navon, G. & Pines, A. (1996) *Proceedings of the National Academy of Sciences of the United States of America* 93, 12932-12936.
23. Hellberg, P. O. A., Bayati, A., Kallskog, 0. & Wolgast, M. (1990) *Kidney International* 37, 1240-1247.
24. Butler, J. P., Mair, R. W., Hoffmann, D., Hrovat, M. I., Rogers, R. A., Topulos, G. P., Walsworth, R. L. & Patz, S. (2002) *Journal of Physics—Condensed Matter* 14, L297-L304.
25. Gewalt, S. L., Glover, G. H., MacFall, J. R., Hedlund, L. W. & Johnson, G. A. (1993) *Magn Reson Med* 29, 99-106.
26. Bergin, C. J., Pauly, J. M. & Macovski, A. (1991) *Radiology* 179, 777-781.
27. Dixon, W. T. (1984) *Simple proton spectroscopy imaging Radiology* 153, 189-194.
28. Bernstein, M. A., King, K. F. & Zhou, X. J. (2004) *Handbook of MRI Pulse Sequences* (Elsevier Academic Press, San Diego).
29. Thrall, R. S., McCormick, J. R., Jack, R. M., McReynolds, R. A. & Ward, P. A. (1979) *American Journal Of Pathology* 95, 117-&.
30. Driehuys, B., Cates, G. D., Miron, E., Sauer, K., Walter, D. K. & Happer, W. (1996) *Applied Physics Letters* 69, 1668-1670.
31. Kuzma, N. N., Patton, B., Raman, K. & Happer, W. (2002) *Physical Review Letters* 88, 147602.
32. Chen, B. T., Brau, A. C. S. & Johnson, G. A. (2003) *Magn Reson Med* 49, 78-88.
33. Johnson, G. A., Cates, G., Chen, X. J., Cofer, G. P., Driehuys, B., Happer, W., Hedlund, L. W., Saam, B., Shattuck, M. D. & Swartz, J. (1997) *Magnetic Resonance in Medicine* 38, 66-71.
34. Zhao, L., Mulkern, R., Tseng, C. H., Williamson, D., Patz, S., Kraft, R., Walsworth, R. L., Jolesz, F. A. & Albert, M. S. (1996) *Journal of Magnetic Resonance Series B* 113, 179-183.
35. Chen, X. J., Hedlund, L. W., Moller, H. E., Chawla, M. S., Maronpot, R. R. & Johnson, G. A. (2000) *Proceedings of the National Academy of Sciences of the United States of America* 97, 11478-11481.
36. Salerno, M., de Lange, E. E., Altes, T. A., Truwit, J. D., Brookeman, J. R. & Mugler, J. P. (2002) *Radiology* 222, 252-260.
37. Ward, E. R., Hedlund, L. W., Kurylo, W. C., Wheeler, C. T., Cofer, G. P., Dewhirst, M. W., Marks, L. B. & Vujaskovic, Z. (2004) *International Journal Of Radiation Oncology Biology Physics* 58, 1562-1569.
38. King, T. E. (2005) *American Journal Of Respiratory And Critical Care Medicine* 172, 268-279.
39. Raghu, G., Mageto, Y. N., Lockhart, D., Schmidt, R. A., Wood, D. E. & Godwin, J. D. (1999) *Chest* 116, 1168-1174.
40. Bjoraker, J. A., Ryu, J. H., Edwin, M. K., Myers, J. L., Tazelaar, H. D., Schroeder, D. R. & Offord, K. P. (1998) *American Journal Of Respiratory And Critical Care Medicine* 157, 199-203.
41. Gewalt S L, Glover G H, MacFall J R, Hedlund L W, Johnson G A. MR microscopy of the rat lung using projection reconstruction. Magn Reson Med 1993; 29:99-106.
42. Song J, Liu Q H, Gewalt S, Cofer G P, Johnson G A. 2D and 3D Projection-Reconstruction MRI Image Reconstruction through Nonuniform Fast Fourier Transform. IEE Trans Med Imag 2005; submitted.
43. Skinner T E, Glover G H. An extended two-point dixon algorithm for calculating separate water, fat, and B-0 images. Magnetic Resonance In Medicine 1997; 37(4): 628-630.
44. Glover G H, Schneider E. 3-Point Dixon Technique For True Water Fat Decomposition With Bo Inhomogeneity Correction. Magnetic Resonance In Medicine 1991; 18(2):371-383.

That which is claimed:

1. A method of generating a three-dimensional $^{129}$Xe MRI image of a lung, comprising:
   conducting an MRI scan of a patient to whom hyperpolarized $^{129}$Xe gas has been administered with one or two breath-holds; and
   generating at least one three-dimensional image of a gas exchange region of at least one lung of a patient using dissolved phase hyperpolarized $^{129}$Xe MRI signal data associated with each of RBC and blood-gas barrier compartments.

2. A method according to claim 1, further comprising employing radial projection encoding with phase-sensitive image reconstruction to generate the three-dimensional image.

3. A method according to claim 1, wherein the generating step comprises acquiring the dissolved phase $^{129}$Xe signal data at multiple repetition times to determine barrier thickness and/or $^{129}$Xe diffusion.

4. A method according to claim 1, further comprising generating sufficient RBC and barrier $^{129}$Xe signal data to curve fit signal replenishment on a pixel-by-pixel basis.

5. A method according to claim 1, wherein the generating the at least one three-dimensional image comprises using a one-point Dixon evaluation of the dissolved phase $^{129}$Xe signal data comprising both RBC signal data and barrier signal data, and wherein there is about a 90 degree phase difference between the dissolved phase hyperpolarized $^{129}$Xe MRI signal data of the RBC compartment and the blood-gas barrier compartment.

6. A method according to claim 1, wherein the generating comprises:
- obtaining a gas-phase hyperpolarized $^{129}$Xe MRI image of the patient;
- electronically generating a field map of spatially varying field shifts corresponding to magnetic field inhomogeneity associated with an MRI scanner using image data of based on the obtained gas-phase $^{129}$Xe MRI image of the patient; and
- electronically correcting phase of the dissolved phase $^{129}$Xe signal data of the RBC and blood-gas barrier compartments using the generated field-map.

7. A method according to claim 1, wherein the generating the at least one three-dimensional image of the gas exchange region of at least one lung of the patient comprises generating 3-D image visualizations of the gas exchange region of the lung with features shown with differing intensity and/or color using the $^{129}$Xe dissolved phase signal data, and wherein the method further comprises displaying the generated 3-D visualizations.

8. A method according to claim 1, further comprising, before the generating step, obtaining the dissolved phase hyperpolarized $^{129}$Xe MRI signal data of (i) the RBC compartment at a first resonance and (ii) the blood-gas barrier compartment at a second resonance different from the first resonance, and wherein the obtaining is carried out using an MRI scanner frequency for $^{129}$Xe dissolved phase imaging that excites both the first and second resonances but not a gas phase resonance of the hyperpolarized $^{129}$Xe.

9. The method of claim 1, further comprising obtaining gas phase $^{129}$Xe signal data of the at least one lung of the patient and correcting the dissolved phase $^{129}$Xe signal data associated with inhomogeneities of a magnetic field of the MRI scanner using the obtained gas phase $^{129}$Xe signal data.

10. The method of claim 1, further comprising directing an MRI scanner to use a scanning sequence for conducting the MRI scan that automatically switches an MRI scanner frequency between a tuned frequency for obtaining $^{129}$Xe gas phase signal to a different tuned frequency for obtaining the $^{129}$Xe dissolved phase signal data of the RBC and blood gas barrier compartments at respective first and second resonances, then back to the tuned frequency for the $^{129}$Xe gas phase signal to thereby acquire hyperpolarized $^{129}$Xe gas and dissolved signal data sets in an interleaved manner.

11. The method of claim 1, wherein the generating the at least one three-dimensional image of the gas exchange region of at least one lung of the patient comprises generating visualizations of the gas exchange region of the lung with differences in barrier thickness shown with differing color over an image volume using the $^{129}$Xe dissolved phase signal data, and wherein the method further comprises displaying the generated visualizations.

12. The method of claim 11, wherein the generated visualizations depict mismatch of RBC replenishment with barrier replenishment of the obtained dissolved phase $^{129}$Xe signal data as an indicator of lung injury.

13. A method of generating visualizations of at least one lung of a patient, comprising:
- conducting an MRI scan of a patient to whom hyperpolarized $^{129}$Xe gas has been administered with one or more breath-holds using an MRI scanner;
- obtaining dissolved phase hyperpolarized $^{129}$Xe signal data for each of RBC and blood-gas barrier compartments of a gas exchange region of at least one lung of a patient;
- generating three-dimensional visualizations of the at least one lung with features shown with differing colors over an image volume of the gas exchange region of the lung using the obtained dissolved phase hyperpolarized $^{129}$Xe signal data of the gas exchange region of at least one lung to thereby depict pulmonary gas transfer abnormalities; and
- displaying the generated visualizations of the at least one lung.

14. The method of claim 13, further comprising correcting the obtained dissolved phase $^{129}$Xe signal data associated with inhomogeneities of a magnetic field of the MRI scanner using obtained gas phase $^{129}$Xe signal data of the patient.

15. The method of claim 13, further comprising directing the MRI scanner to use a scanning sequence for conducting the MRI scan that automatically switches an MRI scanner frequency between a tuned frequency for obtaining $^{129}$Xe gas phase signal data to a different tuned frequency for obtaining the $^{129}$Xe dissolved phase signal data, then back to the tuned frequency for the $^{129}$Xe gas phase to thereby acquire hyperpolarized $^{129}$Xe gas and dissolved signal data sets in an interleaved manner.

16. The method of claim 13, further comprising:
- obtaining gas-phase hyperpolarized $^{129}$Xe signal data of the at least one lung of the patient;
- generating a field map of spatially varying field shifts corresponding to magnetic field inhomogeneity associated with the MRI scanner used for obtaining the dissolved phase $^{129}$Xe signal data using the obtained gas-phase hyperpolarized $^{129}$Xe signal data; and
- correcting phase of the obtained dissolved phase hyperpolarized $^{129}$Xe signal data of the RBC and blood-gas barrier compartments using the generated field-map to generate the visualizations of the gas exchange region of the lung.

17. The method of claim 13, wherein the generated visualizations depict mismatch of RBC replenishment with barrier replenishment of the obtained dissolved phase $^{129}$Xe signal data as an indicator of lung injury.

* * * * *

UNITED STATES PATENT AND TRADEMARK OFFICE
CERTIFICATE OF CORRECTION

PATENT NO.        : 10,261,151 B2
APPLICATION NO.   : 15/447321
DATED             : April 16, 2019
INVENTOR(S)       : Driehuys et al.

Page 1 of 1

It is certified that error appears in the above-identified patent and that said Letters Patent is hereby corrected as shown below:

On the Title Page

Item (56) References Cited, OTHER PUBLICATIONS, Page 2, Column 2, Skinner et al. cite: Please correct "$BO$ Images" to read -- $B_0$ Images --

In the Specification

Column 12, Line 66: Please correct "$M_{air}$," to read -- $M_{air}$ --

Column 17, Line 5: Please correct "32 us" to read -- 32 µs --

In the Claims

Column 33, Line 16, Claim 6: Please correct "of based on the obtained" to read -- of the obtained --

Signed and Sealed this
Thirtieth Day of July, 2019

Andrei Iancu
*Director of the United States Patent and Trademark Office*